US008481697B2

(12) United States Patent
Lohse et al.

(10) Patent No.: US 8,481,697 B2
(45) Date of Patent: Jul. 9, 2013

(54) NUCLEIC ACID BASE PAIRS

(75) Inventors: Jesper Lohse, København NV (DK); Kenneth Heesche Petersen, Smørum (DK)

(73) Assignee: Dako Denmark A/S, Glostrup (DK)

( * ) Notice: Subject to any disclaimer, the term of this patent is extended or adjusted under 35 U.S.C. 154(b) by 919 days.

(21) Appl. No.: 11/993,565

(22) PCT Filed: Jun. 30, 2006

(86) PCT No.: PCT/IB2006/003306
§ 371 (c)(1),
(2), (4) Date: Jan. 4, 2010

(87) PCT Pub. No.: WO2007/045998
PCT Pub. Date: Apr. 26, 2007

(65) Prior Publication Data
US 2010/0105030 A1 Apr. 29, 2010

Related U.S. Application Data

(60) Provisional application No. 60/695,408, filed on Jul. 1, 2005, provisional application No. 60/695,409, filed on Jul. 1, 2005, provisional application No. 60/695,410, filed on Jul. 1, 2005.

(51) Int. Cl.
*C07H 21/00* (2006.01)
*C07H 21/02* (2006.01)
*C07H 21/04* (2006.01)
*C12Q 1/68* (2006.01)

(52) U.S. Cl.
USPC .......... 536/23.1; 536/24.3; 536/25.3; 435/6.1

(58) Field of Classification Search
USPC .................. 536/23.1, 24.3, 25.3; 435/6.1
See application file for complete search history.

(56) References Cited

U.S. PATENT DOCUMENTS
2002/0072056 A1 6/2002 Sudo et al.
2004/0033973 A1 2/2004 Manoharan et al.

FOREIGN PATENT DOCUMENTS
WO WO 8902921 * 4/1989
WO WO92/20703 11/1992
WO WO 03/080857 A2 10/2003

OTHER PUBLICATIONS

K. Shohda et al. "Synthesis and properties of 2'-O-methyl-2-thiouridine and oligoribonucleotides containing 2'-O-methyl-2-thiouridine," *Bioorganic & Medicinal Chemistry Letters*, 2000, 10, 1795-1798.
I. Okamoto et al., "A new route to 2'-O-alkyl-2-thiouridine derivatives via 4-O-protection of the uracil base and hybridization properties of oligonucleotides incorporating these modified nucleoside derivatives," *J. Organic Chemistry*, 2003, 68, 9971-9982.
T.V.S. Rao et al., "Incoporation of 4-Thiothymidine Into DNA by the Klenow Fragment and HIV-1 Reverse Transcriptase," *Bioorganic & Medicinal Chemistry Letters*, 10: 907-910 (2000).
Communication pursuant to Article 94(3) EPC, mailed Aug. 5, 2011, for European Patent Application No. 06 842 206.2-1211 (4 pages).
International Search Report, mailed Feb. 4, 2008, for International Patent Application No. PCT/IB2006/003306 (11 pages).
International Preliminary Report on Patentability, issued Mar. 4, 2008, for International Patent Application No. PCT/IB2006/003306 (11 pages).
Hyrup, "A flexible and positively charged PNA analogue with an Ethylene-Linker to the Nucleobase: Synthesis and Hybridization Properties", *Bioorganic & Medicinal Chemistry Letters*, vol. 6, No. 10, pp. 1083-1088, 1996.
Kumar, "8-Amino-2'-Deoxyadenosine : 2' Deoxythymidine Base Pairing: Identification to Novel Reverse Hoogsteen Mode in Solution", *Biochemical and Biophysical Research Communications*, vol. 204, No. 2, pp. 788-793, Oct. 28, 1994.
Gassen, "Codon-Anticodon Interaction Studied with Oligonucleotides Containing $_3$-Deazauridine, $_4$-Deoxyuridine or $_3$ Deaza-$_4$-Deoxyuridine II Ribosome Binding of Oligonnucleotides and Phenylalanyl-tRNA", *Biochem. Biophys. Acta*, vol. 272, pp. 560-567, 1972.
Warren, "Synthesiss and Chracterisation of Oligodeoxynucleotides Containing Thio Analogues of (6-4) Pyrimidine-Pyrimidinone Photo-dimers", *J. Mol. Biol.*, vol. 279, pp. 89-100, 1998.
Rappaport, "The 6-thioguanine/5-methyl-2-pyrimidinone base pair", *Nucleic Acids Research*, vol. 16, No. 15, pp. 7253-7267, 1988.
Tanaka, "Synthesis and Properties of Phosphoramidite Derivatives of Modified Nucleosides", *Chem. Pharm. Bull.*, vol. 34, pp. 2044-2048, 1986.
Kirnos, "2-Aminoadenine is an adenine substituting for a base in S-2L cyanophage DNA", *Nature*, vol. 270, No. 24, pp. 369-370, Nov. 1977.
Gaffney, "The influence of the Purine 2-Amino Group on DNA Conformation and Stability—II", *Tetrahedron*, vol. 40, No. 1, pp. 3-13, 1984.
Kikuchi, "Evaluation of the 2 NH$_2$A-T Pair in Hybridization, I Synthesis of the DNA/RNA Hybrid Oligomers Containing 2-Aminoadenosines", *Z. Natufforsch*, vol. 43b, pp. 623-630, 1988.
Response to Communication A94(3) EPC, mailed May 24, 2012, for European Application No. 06842206.2-1211 (17 pages).
Response to Communication R.161 and R.162 EPC, mailed Jun. 30, 2008, for European Application No. 06842206.2-1211 (31 pages).

* cited by examiner

*Primary Examiner* — Jezia Riley
(74) *Attorney, Agent, or Firm* — Finnegan, Henderson, Farabow, Garrett & Dunner L.L.P.

(57) ABSTRACT

The invention relates to non-natural bases and base pairs that expand the normal DNA-based encoding system. Compositions herein may comprise at least one non-natural base that may interact with another base via a Watson Crick-type hydrogen bonding geometry and/or a Hoogsteen-type hydrogen bonding geometry. The bases may be used in a molecular entity, such as an oligomer or any other entity wherein the bases are attached to a backbone. For example, they may be comprised in DNA, RNA, or PNA, or a variety of other nucleic acid-type systems.

21 Claims, 16 Drawing Sheets

Figure 1
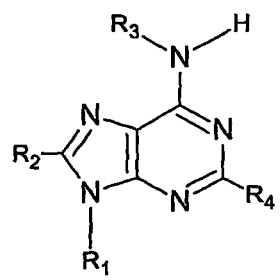
Figure 1a, Adenine, A
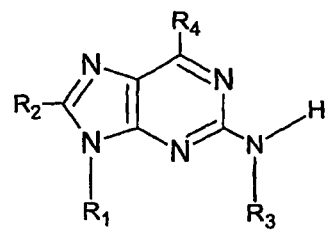
Figure 1b, isoAdenine, isoA
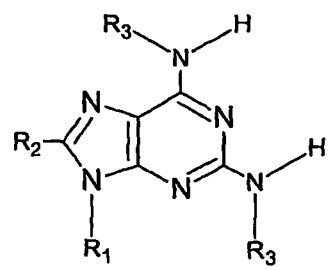
Figure 1c, Diaminopurine, D

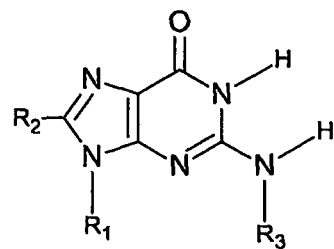
Figure 1d, Guanine, G
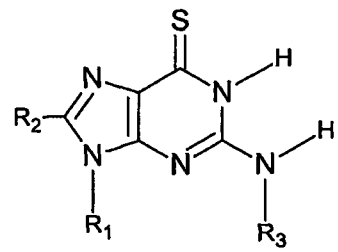
Figure 1e, ThioGuanine, Gs
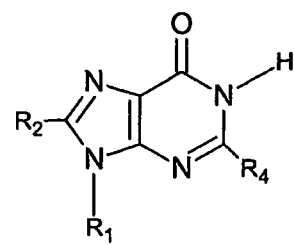
Figure 1f, Inosine, I
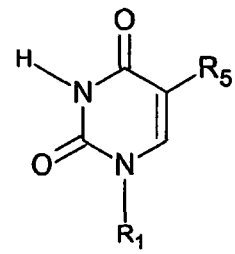
Figure 1g, Uracil, U

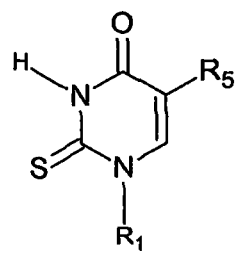
Figure 1h, 2-ThioUracil, U2s
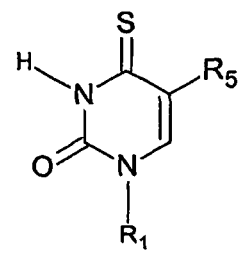
Figure 1i, 4-ThioUracil, U4s
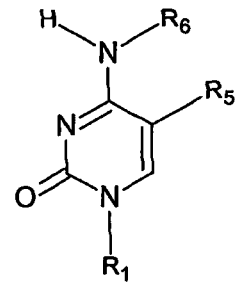
Figure 1j, Cytosine, C
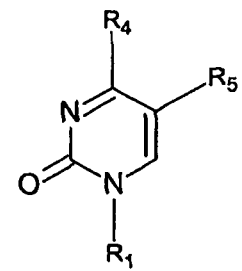
Figure 1k, 2-oxo-Pyrimidine, Py-2o

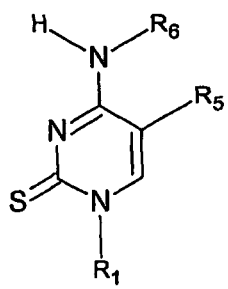
Figure 1l, ThioCytosine, Cs
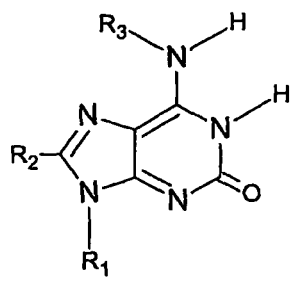
Figure 1m, isoGuanine, isoG
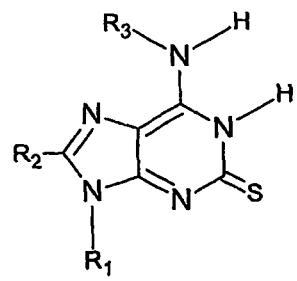
Figure 1n, isothioGuanine, isoGs
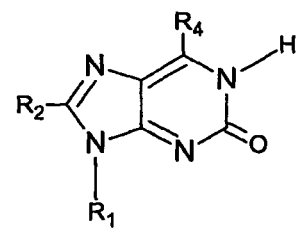
Figure 1o, 2-oxoPurine, Pu-2o

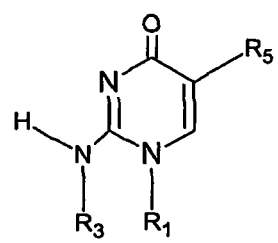
Figure 1p, isoCytosine, isoC
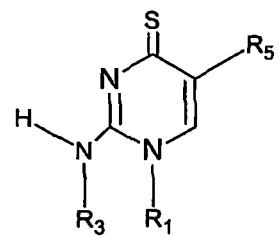
Figure 1q, isothioCytosine, isoCs
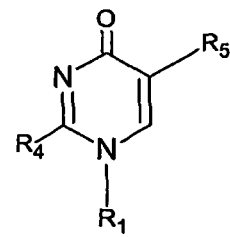
Figure 1r, 4-oxoPyrimidine, Py-4o

Figure 2
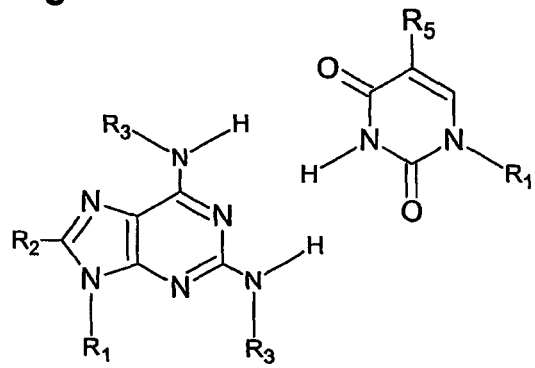
Figure 2a Diaminopurine-Uracil
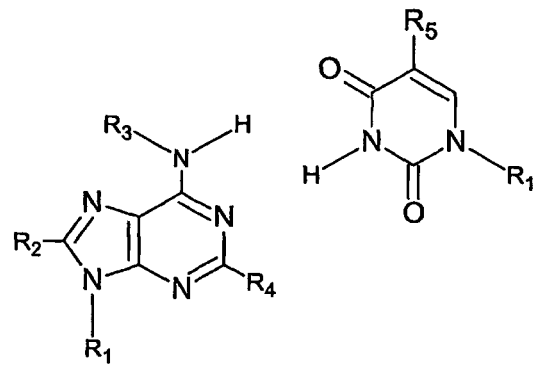
Figure 2b Adenine-Uracil
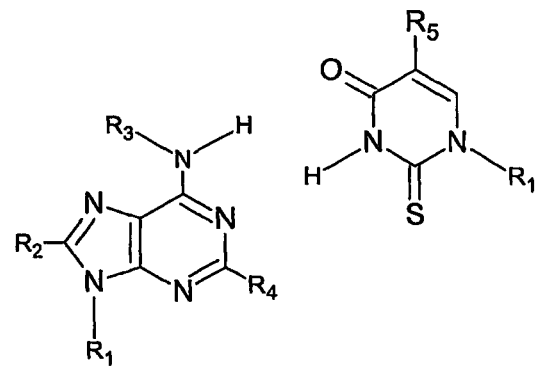
Figure 2c Adenine-2-thioUracil

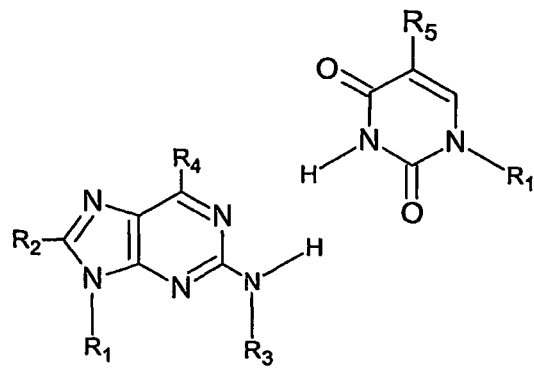
Figure 2d IsoAdenine-Uracil
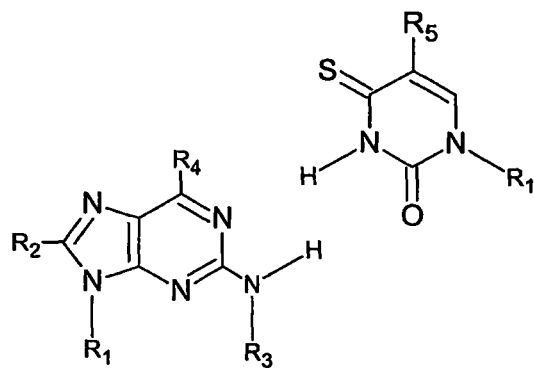
Figure 2e IsoAdenine-4thioUracil
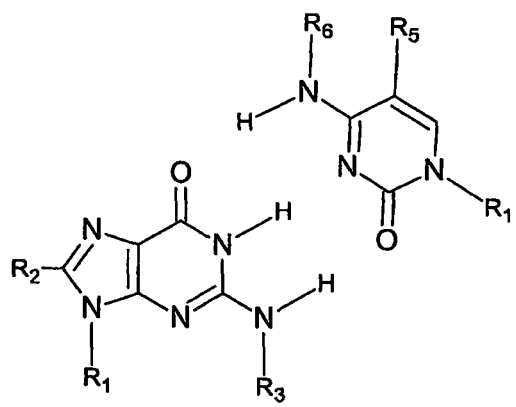
Figure 2f Guanine-Cytosine

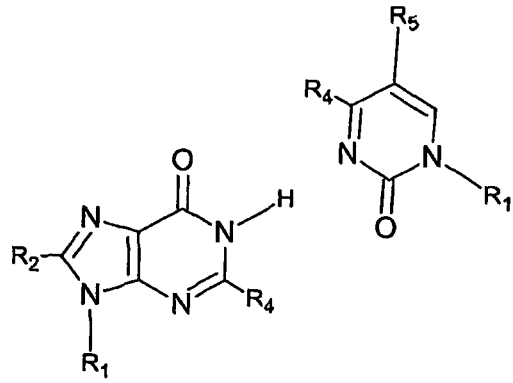
Figure 2g Guanine-2-oxo-Pyrimidine
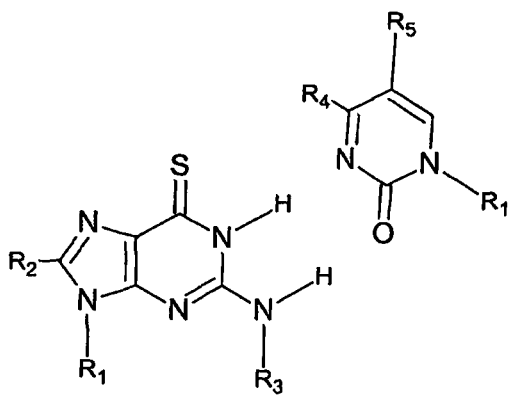
Figure 2h ThioGuanine-2-oxo-Pyrimidine
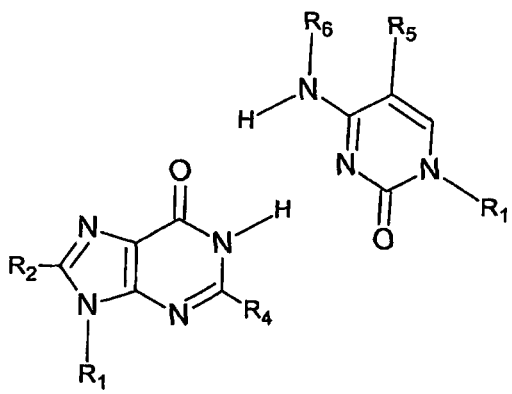
Figure 2i Inosine-Cytosine

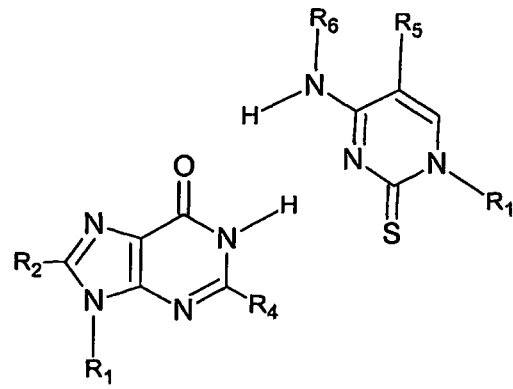
Figure 2j Inosine-ThioCytosine
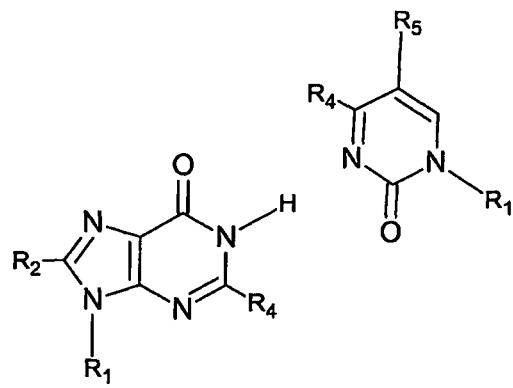
Figure 2k Inosine-2-oxo-Pyrimidine
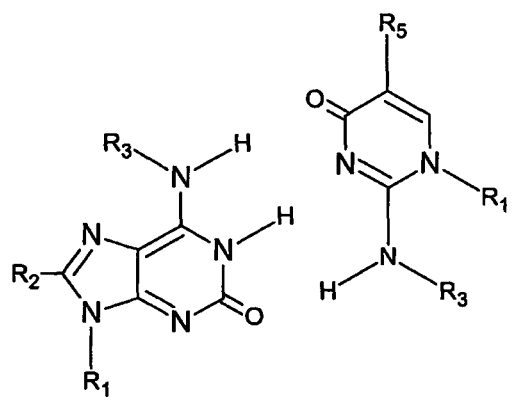
Figure 2l IsoGuanine-IsoCytosine

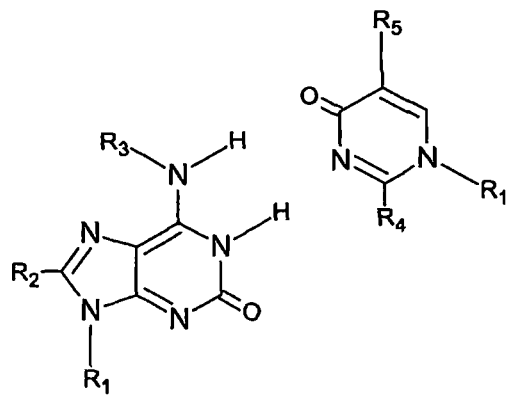
Figure 2m isoGuanine-4-oxo-Pyrimidine
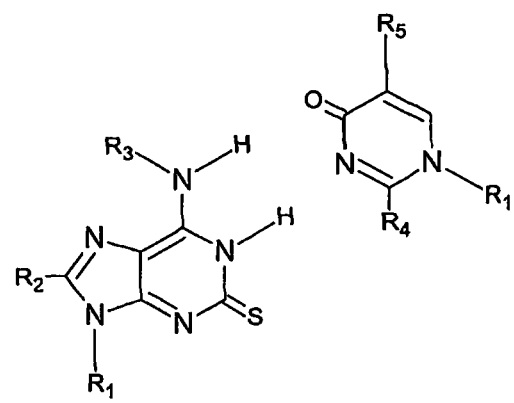
Figure 2n isothioGuanine-4-oxo-pyrimidine
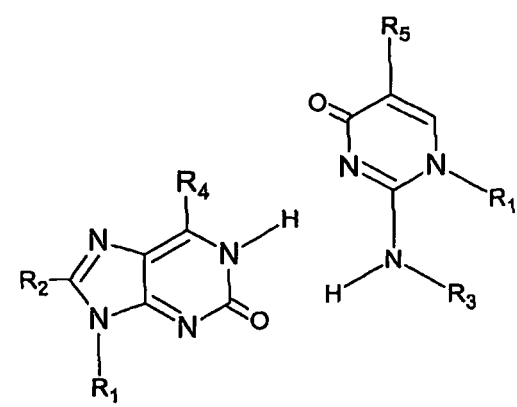
Figure 2o 2-oxo-Purine-isoCytosine

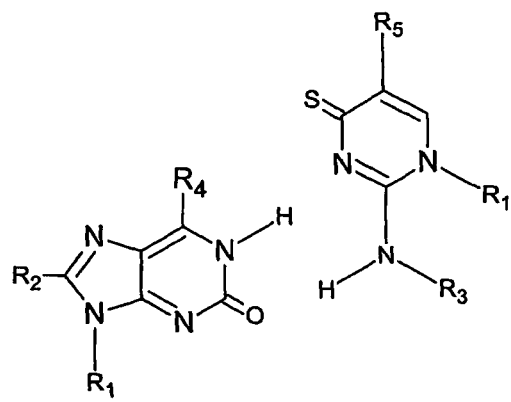
Figure 2p 2-oxo-Purine-isothioCytosine
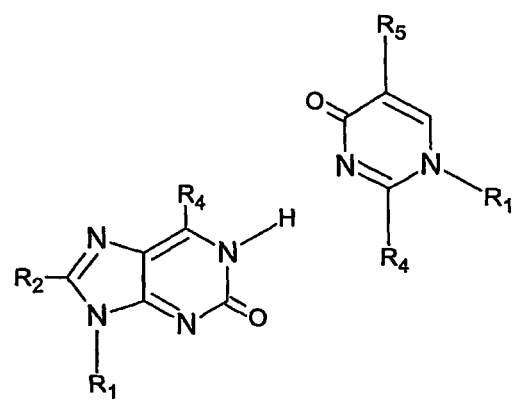
Figure 2q 2-oxo-Purine-4-oxo-Pyrimidine

Figure 3

| Base Pairs | Diaminopurine | Adenine |
|---|---|---|
| Uracil | 3 H-bonds | 2 H-bonds |
| 2-ThioUracil | repulsion | 2 H-bonds |

| Base Pairs | Diaminopurine | isoAdenine |
|---|---|---|
| Uracil | 3 H-bonds | 2 H-bonds |
| 4-ThioUraci | repulsion | 2 H-bonds |

| Base Pairs | Guanine | Inosine |
|---|---|---|
| Cytosine | 3 H-bonds | 2 H-bonds |
| 2-ThioCytosine | repulsion | 2 H-bonds |

| Base Pairs | Cytosine | 2-oxo-Pyrimidine |
|---|---|---|
| Guanine | 3 H-bonds | 2 H-bonds |
| ThioGuanine | repulsion | 2 H-bonds |

| Base Pairs | isoGuanine | 2-oxo-Purine |
|---|---|---|
| isoCytosine | 3 H-bonds | 2 H-bonds |
| isoThioCytosine | repulsion | 2 H-bonds |

| Base Pairs | isoCytosine | 4-Oxo-Pyrimidine |
|---|---|---|
| isoGuanine | 3 H-bonds | 2 H-bonds |
| isoThioGuanine | repulsion | 2 H-bonds |

Figure 6

|  | Adenines | 8-aminopurines | 2,6-diaminopurines | Guanines | Inosines | 6-Thioguanines | Isoguanines | Iso-2-thioguanines | 2-oxo-purines | Uracils | 2-thioxouracils | 4-thioxouracils | Cytosine | 2-thioxocytosine | 2-oxo-pyrimidines | Isocytosine | Iso-4-thioxocytosine | 4-oxo-pyrimidines |
|---|---|---|---|---|---|---|---|---|---|---|---|---|---|---|---|---|---|---|
| Adenines |  |  |  |  |  |  |  |  |  | 2 | 2 |  |  |  |  |  |  |  |
| 8-aminopurines |  |  |  |  |  |  |  |  |  | 2 |  |  |  |  |  |  |  |  |
| 2,6-diaminopurines |  |  |  |  |  |  |  |  |  | 3 |  |  |  |  |  |  |  |  |
| Guanines |  |  |  |  |  |  |  |  |  |  |  | 3 |  |  |  |  |  |  |
| Inosines |  |  |  |  |  |  |  |  |  |  |  | 2 | 2 |  |  |  |  |  |
| 6-Thioguanines |  |  |  |  |  |  |  |  |  |  |  |  | 2 |  |  |  |  |  |
| Isoguanines |  |  |  |  |  |  |  |  |  |  |  |  |  |  | 3 |  |  |  |
| Iso-2-thioguanines |  |  |  |  |  |  |  |  |  |  |  |  |  |  |  | 2 | 2 |  |
| 2-oxo-purines |  |  |  |  |  |  |  |  |  |  |  |  |  |  | 2 |  | 2 | 1 |
| Uracils | 2 | 2 | 3 |  |  |  |  |  |  |  |  |  |  |  |  |  |  |  |
| 2-thioxouracils | 2 |  |  |  |  |  |  |  |  |  |  |  |  |  |  |  |  |  |
| 4-thioxouracils |  |  |  | 2 |  |  |  |  |  |  |  |  |  |  |  |  |  |  |
| cytosine |  |  |  | 3 | 2 |  |  |  |  |  |  |  |  |  |  |  |  |  |
| 2-thioxocytosine |  |  |  | 2 | 2 |  |  |  |  |  |  |  |  |  |  |  |  |  |
| 2-oxo-pyrimidines |  |  |  | 2 | 1 |  |  |  |  |  |  |  |  |  |  |  |  |  |
| Isocytosine |  |  |  |  |  |  | 3 | 2 |  |  |  |  |  |  |  |  |  |  |
| Iso-4-thioxocytosine |  |  |  |  |  |  | 2 | 2 |  |  |  |  |  |  |  |  |  |  |
| 4-oxo-pyrimidines |  |  |  |  |  |  |  | 2 | 1 |  |  |  |  |  |  |  |  |  |

NUCLEIC ACID BASE PAIRS

This international application claims priority to three U.S. Provisional Patent Applications, Nos. 60/695,408; 60/695,409; and 60/695,410, each of which was filed on Jul. 1, 2005. Each of those applications is incorporated herein by reference.

This application is a national stage filing under 35 U.S.C. §371 of International Application No. PCT/IB2006/003306 filed on 30 Jun. 2006.

BACKGROUND AND SUMMARY OF THE INVENTION

This invention relates to non-natural bases and base pairs. The bases are an expansion of a DNA based encoding system. For example, the system is based on Watson-Crick type Acceptor:Donor hydrogen bond base pairing patterns.

Mutually complementary pairs of oligomers, such as DNA and PNA, are used in countless applications as molecular labels/recognizers and probes. The diversity of the 4 naturally occurring nucleobases, A, C, G, and T allows a multitude of diverse labels to be constructed (a 10'mer comes in $4^{10}=1$ million versions). Furthermore, the labels are recognized in a modular fashion by Watson-Crick base pairing, where A:::T, G:::C and vice versa, i.e., from the label follows the complementary strand.

The use of DNA and PNA, however, is limited by some inherent drawbacks. For example, DNA, while having several desirable properties such as easy enzymatic or chemical synthesis, is poly anionic with each base contributing with a negatively charged phosphate moiety. Thus, while DNA will hybridize to its complement with high affinity and specificity, it will also bind unspecifically to any poly cationic species such as many proteins, metal ions and surfaces.

Since PNA is a non charged polypeptide oligomer, it does not exhibit such unspecific affinity for poly cations or poly anions. However, the lack of charge gives generally lower solubility and increases inter and intra-molecular interactions and tends to make PNA highly self-aggregating.

Also limiting the use of a base pairing oligomer is it's self-structure. DNA strands of even moderate length will form intramolecular hairpins and other complex structures that basically hide the bases from recognition by the complementary oligomer. This is especially pronounced for PNAs where charge-charge repulsions do not tend to straighten the backbone. The self structure may significantly slow down the rate of and can even ultimately prevent the desired hybridization between complementary strands.

The problem may be further augmented when for amplification purposes more than one label-PNA/DNA is attached to the same probe. Intermolecular interactions may then contribute to aggregation and formation of undesirable complexes that are not readily available for recognition by the complementary strand.

Additionally, in most samples, more than one potential target will be present. For example, in almost any bioassay, there will be RNA and/or DNA present. Thus, the probes may interact specifically yet undesirably with RNA and DNA present in the sample producing false results. Even PNA, which by merit of its higher self-affinity than DNA/RNA might specifically recognize complementary PNA even in the presence of competing DNA/RNA, is limited by a very slight difference in discrimination.

The inventor has found that by increasing the number of bases, complementary labels with varying mutual affinity can be obtained. The affinity may also be modulated by the use of strong 3 hydrogen bond G:::C-type base pairs over weaker 2 hydrogen bond A::T-type base pairs. This is in sharp contrast to molecular recognition via proteins where there are no similar simple rules governing complex interactions. It has also been discovered that increasing the number of bases may overcome at least one of the drawbacks outlined above.

Compositions are disclosed that comprise at least one non-natural base. Bases used herein include the natural bases, A, G, T, C, and U, and the purine-like and pyrimidine-like molecules disclosed herein and any other non-natural base that may interact with another base via a Watson Crick-type, wobble, and/or Hoogsteen-type hydrogen bonding geometry. The bases may be used in a molecular entity, such as an oligomer or other entity where the bases are attached to a backbone. For example, they may be comprised in oligomers of DNA/RNA or PNA.

The non-natural bases of the invention may be chosen from the purine-like molecules and the pyrimidine-like molecule disclosed herein. In one embodiment, a composition is disclosed comprising at least one molecular entity which comprises a set of molecules comprising at least one non-natural base, such as, for example, at least one purine-like molecule and at least one pyrimidine-like molecule. The molecular entity, may for example, be double stranded and the backbone of each strand may be the same or different.

The interaction between the at least one purine-like molecule and the at least one pyrimidine-like molecule may comprise two or three hydrogen bonds. For example, the interaction between the at least one purine-like molecule and the at least one pyrimidine-like molecule may comprise an interaction chosen from a Watson Crick-type wobble and a Hoogsteen-type hydrogen bonding geometry. Bases on an entity may also be chosen and/or paired with other bases where there are single interactions, no interactions or repulsions. This may enable one to fine tune the affinity of the bases for one another.

Another embodiment is a method of labeling a biological substance comprising the step of binding at least one composition of the invention to the biological substance. Also disclosed is a method of binding at least one first molecular entity to at least one second molecular entity comprising bringing into contact, at least one purine-like molecule from the at least one first molecular entity with at least one pyrimidine-like molecule from the at least one second molecular entity, wherein, the at least one purine-like molecule interacts with the at least one pyrimidine-like molecule such that the interaction comprises at least one hydrogen bond.

A method of detecting the presence of at least one molecular entity is also disclosed which comprises exposing the at least one molecular entity to at least one probe where at least one purine-like molecule from the at least one molecular entity interacts with at least one pyrimidine-like molecule from the at least one probe, or at least one pyrimidine-like molecule from the at least one molecular entity interacts with at least one purine-like molecule from the at least one probe; wherein the at least one purine-like molecule interacts with the at least one pyrimidine-like molecule such that the interaction comprises at least one hydrogen bond.

Methods of making the compositions of the invention and methods of designing probes using the non-natural bases of the invention are also disclosed.

Additional objects and advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

BRIEF DESCRIPTION OF THE FIGURES

FIG. 1 (*a-r*): Examples of the bases of the invention and their names and symbols. Where:
R1 denotes the attachment point to the backbone.
R2 is, for example, substituents in the 8-position of purines: such as hydrogen, halogens, or other small substituents i.e., methyl, ethyl.
R3 is, for example, substituents on hydrogen bonding exocyclic amino groups on bases other than cytosine: such as hydrogen, methyl, ethyl, acetyl.
R4 is, for example, substituents that face a carbonyl in place of an aminogroup: such as hydrogen, fluorine and chlorine.
R5 is, for example, substituents in the 5-position of pyrimidines: for example, fluorofors, hydrogen, halogens, and substituted and unsubstituted groups of C1-C20. This position, for example, allows bulky substituents, if desired.
R6 is, for example, substituents on the hydrogen bonding excocylic amino group of cytosine. This position also allows bulky substituents, for example, alkyl, acyl, and substituted and unsubstituted groups of C1-C20.

FIG. 2 (*a-q*): Examples of base pairs of the invention. Where:
R1 denotes the attachment point to the backbone.
R2 is, for example, substituents in the 8-position of purines: such as hydrogen, halogens, or other small substituents i.e., methyl, ethyl.
R3 is, for example, substituents on hydrogen bonding exocyclic amino groups on bases other than cytosine: such as hydrogen, methyl, ethyl, acetyl.
R4 is, for example, substituents that face a carbonyl in place of an aminogroup: such as hydrogen, fluorine and chlorine.
R5 is, for example, substituents in the 5-position of pyrimidines: for example, fluorofors, hydrogen, halogens, and substituted and unsubstituted groups of C1-C20. This position, for example, allows bulky substituents, if desired.
R6 is, for example, substituents on the hydrogen bonding excocylic amino group of cytosine. This position also allows bulky substituents, for example, alkyl, acyl, and substituted and unsubstituted groups of C1-C20.

FIG. 3: Examples of the pairing of base pairs of FIGS. 1 and 2 with the number of hydrogen bonds involved in the pairings.

FIG. 6: Illustrates the interactions between each of the 18 bases shown in FIG. 1: 3 refers to three hydrogen bonds being present between the bases; 2 refers to two hydrogen bonds being present between the bases; 1 is the presence of one hydrogen bond; and X is a repulsion or no H bonding between the pairs. There are 3 three bond base pairs, 12 two bond base pairs, and 2 single bond base pairs.

DETAILED DESCRIPTION OF THE INVENTION

Definitions

Figure 4:
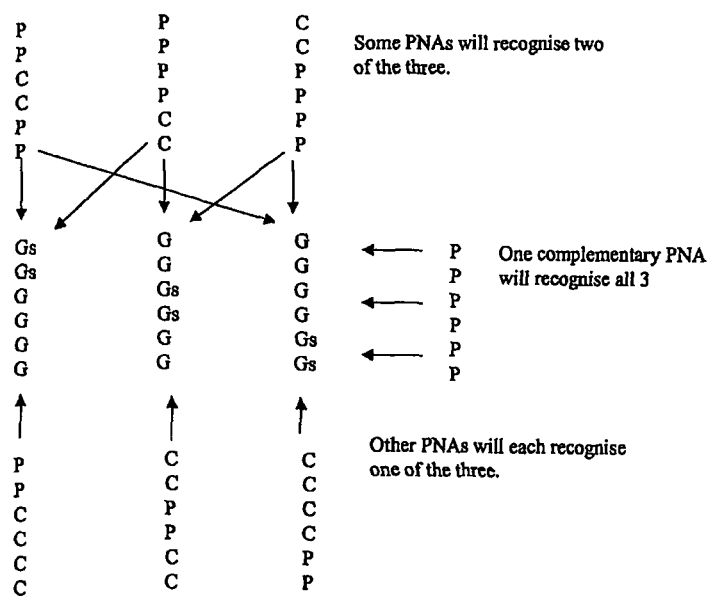
FIG. 4: An Example of 4 sets of probes designed using the base invention. Beginning with the set of probes made of 6'mers of G and Gs (G/Gs probes), a set of probes made of 6'mers of C and P may be designed such that each probe only recognizes one of the G/Gs probes. Another series of 6'mers of C and P may be designed such that some probes will recognize two of the three G/Gs probes. While a 6'mer of P will recognize all three G/Gs probes.

In the descriptions below the following definitions apply.

A linker includes any molecule that may help to join other atoms, molecules, or functional groups together through chemical bonds. A linker may include, for example, any molecule connecting any one of the bases of formula (1)-(16) to a backbone or any molecule that is serves to join another substance to any base or backbone.

A backbone may be any type of polymer including polyamide (e.g., peptide) backbones and sugar-phosphate backbones.

As used herein, the terms base and nucleobase refer to any purine-like or pyrimidine-like molecule that may be comprised in a nucleic acid or nucleic acid analog.

A non-natural base, as used herein, means any nucleobase other than: Adenine, A; Guanine, G; Uracil, U; Thymine, T; Cytosine, C. A non-natural base may also be referred to as a nucleic acid analog with sequences or oligomers, such as two or more of these bases referred to as nucleic acid analog segments.

A group that is optionally substituted may include a substitution with a group chosen from hydroxy, halogen, and —SH.

A molecular entity includes isolated base pair; oligomer entities; polymer entities; double strand entities made of polymers, oligomers, or both; triple strand entities made of polymers, oligomers or both; quad strand entities made of polymers, oligomers or both; single or multi-strand entities made of polymer, oligomer, or both, interacting with isolated molecules; single or multi-strand entities made of polymer, oligomer, or both which includes with folds (such as loops, hairpins, and bulges); helical or helical-like entities and topisomers thereof, coil or coil-like entities and topisomers thereof, superhelical entities (such as toroidal helix, or interwound helix) and topisomers thereof, nicked helix or nicked superhelix entities and topisomers thereof, intercollated helix or superhelix entities and topisomers thereof, right-handed helical entities (such as B-type helices or A-type helices), left-handed helical entities (such as Z form helices) and topisomers thereof.

Base pairs, as used herein, includes any type of hydrogen bonding interaction between two bases and their adjacent backbone, including, but not limited to, geometry such as Watson-Crick, wobble, and Hoogsteen.

Double stranded encompasses a double strand of any type of polymeric backbone and encompasses at least PNA, RNA, and DNA polymer backbones, and includes, but is not limited to, any type of hydrogen-bonded base-pairing geometry such as Watson-Crick, wobble, and Hoogsteen.

Bind or hybridize, and like terms, when referring to natural or non-natural bases includes the formation of base pairs and/or double strands.

Set of, as used herein means at least two of an item.

A probe, as used herein, includes any molecular entity that is capable of recognizing a target substance present in a sample.

As used herein, all numbers are approximate, and may be varied to account for errors in measurement and rounding of significant digits.

Non-Natural Bases

Figure 7:
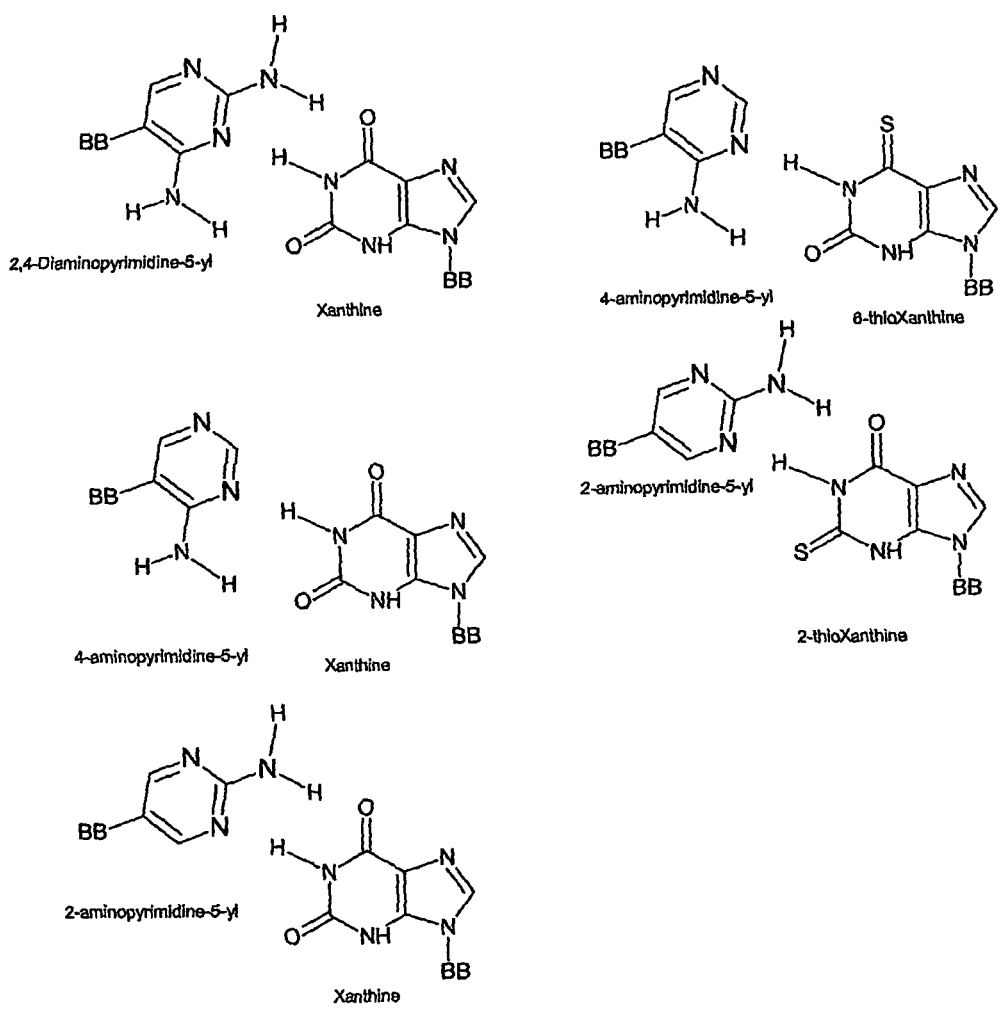
FIG. 7: Illustrates further examples of bases and base-pairs according to the invention, specifically, interactions between a series of base-pairs involving Xanthine, 2-thio-xanthine, and 6-thio-xanthine. 4-aminopyrimidine-5-yl can pair with both Xanthine and 6-thio-xanthine, while 2-aminopyrimidine-5-yl can pair with both Xanthine and 2-thio-xanthine. 2,4-diaminopyrimidine-5-yl only pairs with xanthine.

FIG. 1 provides example bases of the invention. FIG. 7 provides additional examples. In one embodiment, the invention is a general method or principle of generating a diversity of bases and base pairs. For example, the amino group/"h" and carbonyl/thiocarbonyl on either the purine or on the pyrimidine are used to pair the bases. The hydrogen bond in question either facing the minor groove or with the hydrogen bond in question facing the major groove.

Similar to natural bases A, C, G, U, and T, some of the bases disclosed herein are stable three hydrogen bond base pairs between purines and pyrimidines:

Diaminopurine:Uracil; Guanine:Cytosine; isoGuanine: isoCytosine

Substituting one amino group with a Hydrogen or small Halogen (collectively "h") on one of the bases creates six types of bases:
- 2-amino-6-"h"-purines
- 6-amino-2-"h"-purines
- 6-oxo-2-"h"-purines
- 2-oxo-4-"h"-pyrimidines
- 2-oxo-6-"h"-purines
- 4-oxo-2-"h"-pyrimidines These will form two hydrogen bond base pairs with non-thiolated and thiolated bases; respectively
- 2,4 dioxo and 4-oxo-2-thioxo pyrimidines
- 2,4 dioxo and 2-oxo-4-thioxo pyrimidines
- 4-amino-2-oxo and 4-amino-2-thioxo pyrimidines
- 6-oxo-2-amino and 6-thioxo-2-amino purines
- 2-amino-4-oxo and 2-amino-4-thioxo pyrimidines
- 6-oxo-2-amino and 6-thioxo-2-amino purines Whereas
- 4-oxo-2-thioxo pyrimidines will not pair with 2,6-diaminopurines or 2-amino-6-"h"-purines;
- 2-oxo-4-thioxo pyrimidines will not pair with 2,6-diaminopurines or 6-amino-2-"h"-purines;
- 4-amino-2-thioxo pyrimidines will not pair with 2-amino-6-thioxopurines or 2-"h"-6-thioxopurines;
- 6-thioxo-2-amino purines will not pair with 4-amino-2-oxopyrimidines or 4-amino-2-thioxopyrimidines;
- 2-amino-4-thioxo pyrimidines will not pair with 2-thioxo-6-aminopurines or 2-thioxo-6-"h"-purines; and
- 6-thioxo-2-amino purines will not pair with 2-thioxo-6-aminopurines or 2-thioxo-6-"h"-purines.

In each of the above cases, two bases A and B have three mutual hydrogen bonds and form a very stable mutual pair. By substituting one of the hydrogen bonding amino groups on one of the bases, say A, with hydrogen or a small halogen, we get a new base C, and by substituting the facing carbonyl on B, we get a thiocarbonylated base D.

C will now pair with both B and D, forming two stable, two hydrogen bond pairs. A will however not pair with D (or other analogues of B with a thiocarbonyl facing an amino group in A). For example, 2-ThioUracil does not pair with Diaminopurine but pairs with Adenine, while Adenine pairs with both Uracil and 2-ThioUracil, i.e. these 4 bases follow the described pattern, A=Diaminopurine, B=Uracil, C=Adenine, D=2-ThioUracil.

These bases can be used to create molecular entities such as pairs of oligomers that pair well with each other and the number of hydrogen bonds or affinity of the base pairs can be used to fine tune affinity. In one embodiment, these entities result in reduced self structure and increased diversity with Uracils facing Diaminopurines or Adenines and Adenines further facing 2-Thiouracils. It was also surprising that 2-Oxo-pyrimidine pairs with both Guanine and ThioGuanine.

In one embodiment, the bases of the invention can be defined as C, D, G, U from FIG. 1 and their derivatives, such as for example, one carbonyl-thiocarbonyl substitution (Cs, Gs, U2s, and U4s) or one deamination (A, isoA, I (inosine) and P (pyrimidinone)).

Also disclosed is an example set of base pairing rules which one may use as a guide to design additional bases or molecular entities or probes that interact. 1) When part of complementary entities or oligomers, the base pairs obey Watson-Crick rules with hydrogen donors pairing with hydrogen acceptors, via hydrogen bonds, for example, pairing purine bases with pyrimidine bases. For example, C:G share three mutual hydrogen bonds and are thus very stable, while A:U share two mutual hydrogen bonds and contribute to complex stability.

2) Thiocarbonyls, such as on Cs, due to their increased size, repel bases with facing aminogroups, despite two other mutual hydrogen bonds (disallowing, for example, D:U2s and D:U4s) but may pair via two hydrogen bonds with bases that have a hydrogen facing the thiocarbonyls, allowing additional base pairs that also contribute to complex stability, such as Cs:I.

3) Some base pairs, such as I:P, only share a single central hydrogen bond, such as I:P, and is expected to be significantly weaker.

These rules provide an information encoding system that is expanded in comparison to use of natural base in that bases pair with either one (Cs, Gs, U2s, U4s, D), two (A, IsoA, C, G) or three other bases (I, P, U) with the same (A:U2s=A:U) or different affinity (D:U>A:U). Thus, for example, within the same reading frame the system allows multiple different PNAs to be recognized with the same affinity by one other PNA complementary to all of the PNAs, yet also allow each PNA to be recognized with unique specificity by other complementary, yet different PNAs.

The non-natural bases of the invention can be made using synthesis techniques well known in the art. Examples are provided in the examples section below.

Molecular Entities Defined from a Single Base

Disclosed herein are compositions comprising at least one molecular entity which comprises at least one molecule chosen from:

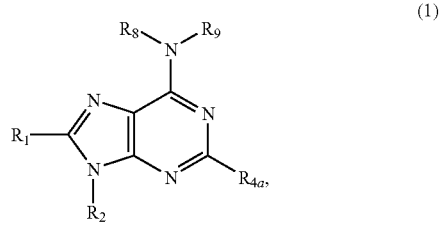

(1)

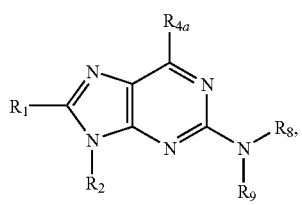 (2)
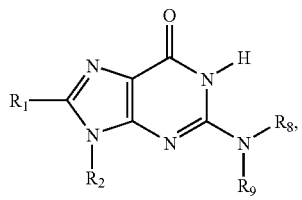 (3)
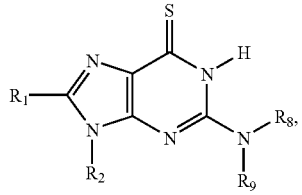 (4)
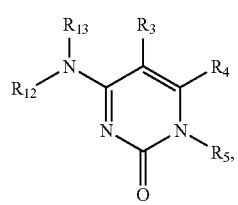 (5)
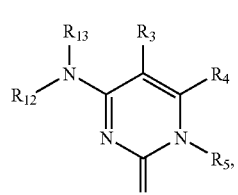 (6)
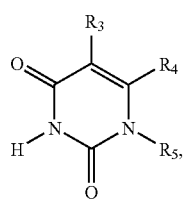 (7)
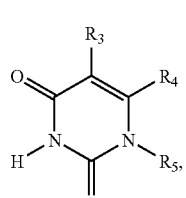 (8)
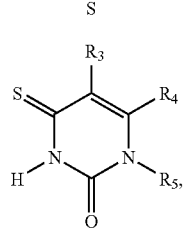 (9)
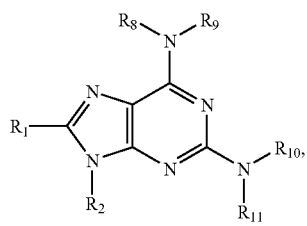 (10)
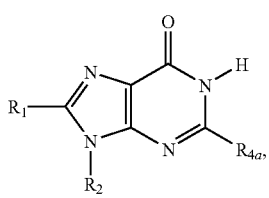 (11)
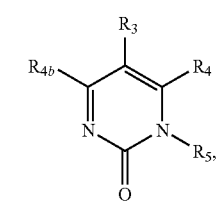 (12)
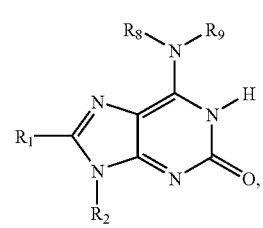 (13)
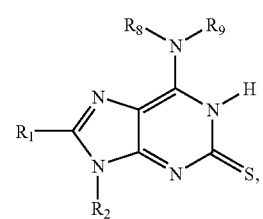 (14)
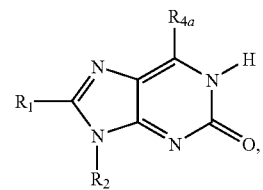 (15)
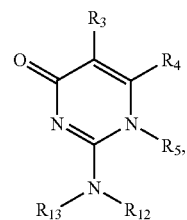 (16)

-continued

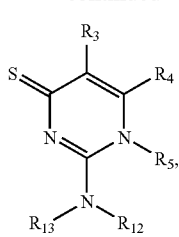
(17)

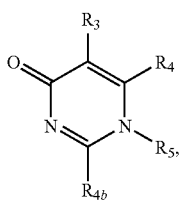
(18)

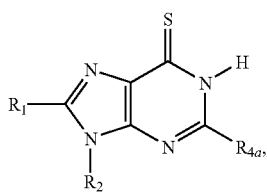
(19)

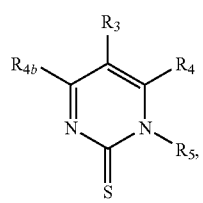
(20)

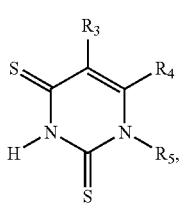
(21)

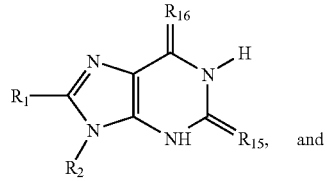
(22)

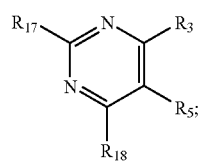 and
(23)

wherein $R_1$ is chosen from hydrogen, halogen, optionally substituted ($C_1$-$C_4$)-alkyl, —$NR_6R_7$, optionally substituted ($C_1$-$C_4$)-alkoxy, optionally substituted ($C_3$-$C_6$)-cycloalkyl, linker, backbone, and linker bound to a backbone;

$R_2$ is chosen from hydrogen, optionally substituted ($C_1$-$C_4$)-alkyl, —$NR_6R_7$, optionally substituted ($C_1$-$C_4$)-alkoxy, optionally substituted ($C_3$-$C_6$)-cycloalkyl, linker, backbone, and linker bound to backbone;

$R_3$ is group chosen from hydrogen, halogen, optionally substituted ($C_1$-$C_{20}$)-alkyl, —$NR_6R_7$, optionally substituted ($C_1$-$C_{20}$)-alkoxy, optionally substituted ($C_3$-$C_8$)-cycloalkyl, linker, backbone, and linker bound to backbone;

$R_4$ is chosen from hydrogen, halogen, optionally substituted ($C_1$-$C_4$)-alkyl, —$NR_6R_7$, optionally substituted ($C_1$-$C_4$)-alkoxy, optionally substituted ($C_3$-$C_6$)-cycloalkyl, linker, backbone, and linker bound to backbone;

$R_{4a}$ and $R_{4b}$ can be identical or different, and are chosen from hydrogen, fluorine and chlorine.

$R_5$ is chosen from hydrogen, optionally substituted ($C_1$-$C_4$)-alkyl, —$NR_6R_7$, optionally substituted ($C_1$-$C_4$)-alkoxy, optionally substituted ($C_3$-$C_6$)-cycloalkyl, linker, backbone, and linker bound to backbone;

$R_6$ and $R_7$ can be identical or different, and are chosen from hydrogen and optionally substituted ($C_1$-$C_{20}$)-alkyl;

$R_8$, $R_9$, $R_{10}$, $R_{11}$, $R_{12}$, and $R_{13}$ can be identical or different, and are chosen from hydrogen, halogen,

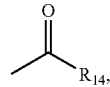

optionally substituted ($C_1$-$C_{20}$)-alkoxy, and optionally substituted ($C_3$-$C_8$)-cycloalkyl, and optionally substituted ($C_1$-$C_{20}$)-alkyl; and $R_{14}$ is chosen from hydrogen, optionally substituted ($C_1$-$C_{20}$)-alkyl, optionally substituted ($C_1$-$C_{20}$)-alkoxy, and optionally substituted ($C_3$-$C_8$)-cycloalkyl;

$R_{15}$ and $R_{16}$ are chosen from oxygen and sulfur;

$R_{17}$ and $R_{18}$ are chosen from hydrogen and —$NH_2$.

In some exemplary embodiments, the at least one molecular entity is not the isolated at least one molecule.

In some exemplary embodiments, $R_1$ is chosen from hydrogen, halogen, methyl and ethyl.

In some exemplary embodiments, $R_2$ is not a phosphate-ribonucleotide backbone, and is not a phosphate-deoxyribonucleotide.

In some exemplary embodiments, $R_1$, $R_3$, and $R_4$ are each is hydrogen.

In some exemplary embodiments $R_3$ is chosen is chosen from optionally substituted ($C_1$-$C_{20}$)-alkyl, —$NR_6R_7$, optionally substituted ($C_1$-$C_{20}$)-alkoxy, optionally substituted ($C_3$-$C_8$)-cycloalkyl, and linker.

In some exemplary embodiments, $R_2$ and $R_5$ can be identical or different and are chosen from linker, backbone, and linker bound to backbone.

In some exemplary embodiments the backbone is chosen from a polyamide backbone and a sugar-phosphate backbone.

In some exemplary embodiments, $R_1$, $R_3$, and $R_4$ each is hydrogen; $R_2$ and $R_5$ can be identical or different radicals and are chosen from backbone and linker bound to backbone; and the backbone is chosen from a polyamide backbone and a sugar-phosphate backbone.

In some exemplary embodiments $R_8$, $R_9$, $R_{10}$, $R_{11}$, $R_{12}$, and $R_{13}$ can be identical or different, and are chosen from hydrogen, halogen,

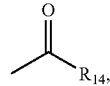

and optionally substituted ($C_1$-$C_4$)-alkyl.

In some exemplary embodiments, $R_{14}$ is chosen from hydrogen, optionally substituted $(C_1-C_4)$-alkyl, optionally substituted $(C_1-C_4)$-alkoxy, and optionally substituted $(C_3-C_6)$-cycloalkyl In some exemplary embodiments $R_8$, $R_9$, $R_{12}$, and $R_{13}$ can be identical or different, and are chosen from hydrogen, methyl ethyl, and acetyl.

In some exemplary embodiments if the at least one molecule is chosen from formula (6), then $R_{12}$ and $R_{13}$ can be identical or different, and are chosen from

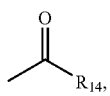

optionally substituted $(C_1-C_{20})$-alkoxy, optionally substituted $(C_3-C_8)$-cycloalkyl, and optionally substituted $(C_1-C_{20})$-alkyl, and $R_{14}$ is chosen from optionally substituted $(C_1-C_{20})$-alkyl, optionally substituted $(C_1-C_{20})$-alkoxy, and optionally substituted $(C_3-C_8)$-cycloalkyl.

In some exemplary embodiments, the at least one molecular entity is double stranded, the backbone of each strand may be the optionally same, and the backbone may be optionally chosen from polyamide backbone and sugar phosphate backbone.

In some embodiments, in the compounds of FIG. 1 and FIG. 2, any of the R groups, R1-R6 present are H, for example, R2=H, R3=H, R4=H, R5=H, and R6=H, if they are present. In another embodiment, any of the R groups R1-R6 present are methyl. In another embodiment, R1 to R6 are independently chosen from H and methyl. For example, some specific embodiments of bases of the invention are the structures shown in FIG. 1 with the following substituents:

| Base (Symbol) | R2 | R3 | R4 | R5 | R6 |
|---|---|---|---|---|---|
| A | H or CH$_3$ | H | H | | |
| isoA | H or CH$_3$ | H | H | | |
| D | H or CH$_3$ | H | | | |
| G | H or CH$_3$ | H | | | |
| Gs | H or CH$_3$ | H | | | |
| I | H or CH$_3$ | | H | | |
| U | | | | H or CH$_3$ | |
| U2s | | | | H or CH$_3$ | |
| U4s | | | | H or CH$_3$ | |
| C | | | | H or CH$_3$ | H |
| Py-2o | | | H or CH$_3$ | H or CH$_3$ | |
| Cs | | | | H or CH$_3$ | H |
| isoG | H or CH$_3$ | H | | | |
| isoGs | H or CH$_3$ | H | | | |
| Pu-2o | H or CH$_3$ | | H | | |
| isoC | | H | | H or CH$_3$ | |
| isoCs | | H | | H or CH$_3$ | |
| Py-4o | | | H or CH$_3$ | H or CH$_3$ | |
| A | H or CH$_3$ | H | CH$_3$ | | |
| isoA | H or CH$_3$ | H | CH$_3$ | | |
| D | H or CH$_3$ | CH$_3$ | | | |
| G | H or CH$_3$ | CH$_3$ | | | |
| Gs | H or CH$_3$ | CH$_3$ | | | |
| I | H or CH$_3$ | | CH$_3$ | | |
| U | | | | H or CH$_3$ | |
| U2s | | | | H or CH$_3$ | |
| U4s | | | | H or CH$_3$ | |
| C | | | | H or CH$_3$ | CH$_3$ |
| Py-2o | | | H or CH$_3$ | H or CH$_3$ | |
| Cs | | | | H or CH$_3$ | CH$_3$ |
| isoG | H or CH$_3$ | CH$_3$ | | | |
| isoGs | H or CH$_3$ | CH$_3$ | | | |
| Pu-2o | H or CH$_3$ | | CH$_3$ | | |
| isoC | | CH$_3$ | | CH$_3$ or CH$_3$ | |
| isoCs | | CH$_3$ | | CH$_3$ or CH$_3$ | |
| Py-4o | | | H or CH$_3$ | H or CH$_3$ | |

In another embodiment, one or more of the H or CH$_3$ are independently substituted with a halogen such as Cl or F. (Note that FIGS. 1 and 2 and the above table use a different numbering of R groups than do the drawings above.)

FIG. 7 illustrates other base pairing schemes compatible with the invention. Those involve Xanthine (X) or 2-thio-xanthine (2X) or 6-thio-xanthine (6X). X pairs with each of 2,4-diaminopyrimidine-5-yl, 2-aminopyrimidine-5-yl, and 4-aminopyrimidine-5-yl, while 2X also pairs with 2-aminopyrimidine-5-yl and 6X also pairs with 4-aminopyrimidine-5-yl. Accordingly, the choice of X or 2X or 6X in one strand opposed to the aminopyrimidine derivatives in the opposite strand allows one to control the level of degeneracy in a nucleic acid sequence. $R_1$ or "BB" in FIG. 1, 2, or 7 may be a point of attachment to a polymer backbone, for instance, a polyamide, DNA, RNA, etc. backbone.

In some embodiments, the following types of base pairs are used: one or more of Us:A, T:D, C:G, and P:Gs. In some embodiments, T:A and P:G are used.

Molecular Entities Defined from Base Pairs

In some embodiments, the bases or base-pairs are chosen from a sub-set of those depicted in FIGS. 1, 2, and 7, depending on the needs of the application. In other exemplary embodiments of the invention, a composition comprising at least one molecular entity which comprises a set of molecules comprising at least one purine-like molecule (such as formulas (1)-(4), (10), (11), (13)-(15), (19), and (22), and salts thereof) and at least one pyrimidine-like molecule (such as formulas (5)-(9), (12), (16)-(18), (20), (21), and (23), and salts thereof) is chosen.

In exemplary embodiments, the set of molecules is chosen from:

(a) at least one purine-like molecule of formula (10) or a salt thereof and at least one pyrimidine-like molecule of formula (7) or a salt thereof;

(b) at least one purine-like molecule of formula (1) or a salt thereof and at least one pyrimidine-like molecule of formula (8) or a salt thereof;

(c) at least one purine-like molecule of formula (2) or a salt thereof and at least one pyrimidine-like molecule of formula (9) or a salt thereof;

(d) at least one purine-like molecule of formula (4) or a salt thereof and at least one pyrimidine-like molecule of formula (12) or a salt thereof;

(e) at least one purine-like molecule of formula (11) or a salt thereof and at least one pyrimidine-like molecule of formula (6) or a salt thereof;

(f) at least one purine-like molecule of formula (1) or a salt thereof and at least one pyrimidine-like molecule of formula (7) or a salt thereof;

(g) at least one purine-like molecule of formula (2) or a salt thereof and at least one pyrimidine-like molecule of formula (7) or a salt thereof;

(h) at least one purine-like molecule of formula (3) or a salt thereof and at least one pyrimidine-like molecule of formula (5) or a salt thereof;

(i) at least one purine-like molecule of formula (3) or a salt thereof and at least one pyrimidine-like molecule of formula (12) or a salt thereof;

(j) at least one purine-like molecule of formula (11) or a salt thereof and at least one pyrimidine-like molecule of formula (12) or a salt thereof;

(k) at least one purine-like molecule of formula (11) or a salt thereof and at least one pyrimidine-like molecule of formula (5) or a salt thereof;

(l) at least one purine-like molecule of formula (13) or a salt thereof and at least one pyrimidine-like molecule of formula (16) or a salt thereof;

(m) at least one purine-like molecule of formula (13) or a salt thereof and at least one pyrimidine-like molecule of formula (18) or a salt thereof;

(n) at least one purine-like molecule of formula (14) or a salt thereof and at least one pyrimidine-like molecule of formula (18) or a salt thereof;

(o) at least one purine-like molecule of formula (15) or a salt thereof and at least one pyrimidine-like molecule of formula (16) or a salt thereof;

(p) at least one purine-like molecule of formula (15) or a salt thereof and at least one pyrimidine-like molecule of formula (17) or a salt thereof;

(q) at least one purine-like molecule of formula (15) or a salt thereof and at least one pyrimidine-like molecule of formula (18) or a salt thereof;

(r) at least one purine-like molecule of formula (22) and at least one pyrimidine-like molecule of formula (23).

In some embodiments, the purine-like and pyrimidine-like molecules are chosen from a subset of the (a) through (r) pairings. For example, certain embodiments may comprise only molecular entities selected from the (r) series, while others may include only those from the (m) series. Other embodiments may exclude certain pairings, such as (m) or (r). Other embodiments may select bases or base pairs from several or all of those listed above but may exclude specific bases, such as, for example, any one, any two, or any larger number of xanthine, 2-thio-xanthine, 6-thio-xanthine, 2,4-diaminopyrimidine-5-yl, 2-aminopyrimidine-5-yl, 4-aminopyrimidine-5-yl, and/or any of the specific bases in the table above. The specific choice of non-natural and natural base-pairs around which to build a sequence may depend on the needs of the application.

In exemplary embodiments, the at least one purine-like molecule interacts with the at least one pyrimidine-like molecule such that the interaction (which can be interstrand or intrastrand) comprises at least one hydrogen bond. In some exemplary embodiments, the hydrogen bonds can be part of Watson Crick or Watson-Crick-like hydrogen bonding geometry, or part of Hoogsteen or Hoogsteen-like hydrogen bonding geometry.

Other exemplary embodiments include those of the previous section.

In other exemplary embodiments the set of molecules is chosen from the following pairings, shown in an example orientation with respect to one another:

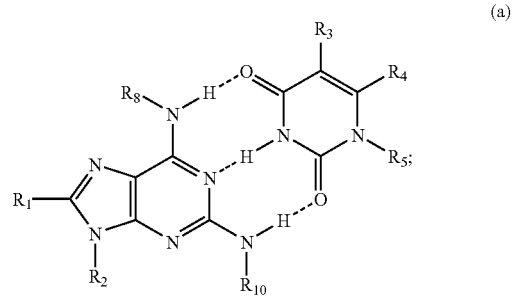

(a)

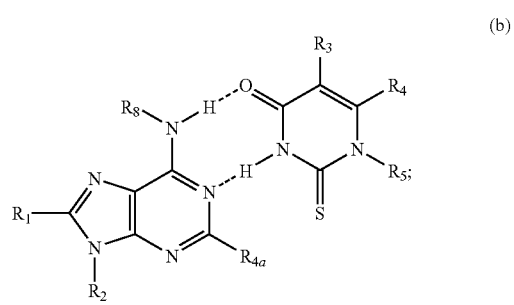

(b)

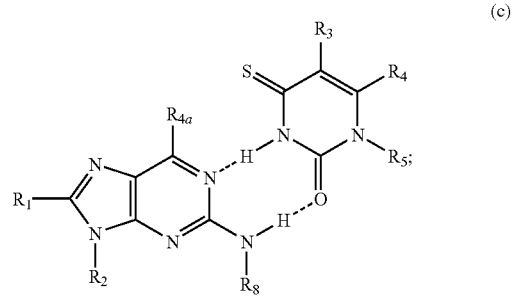

(c)

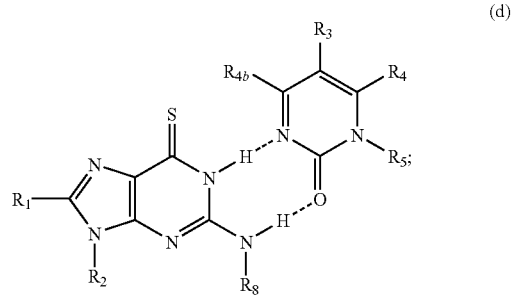

(d)

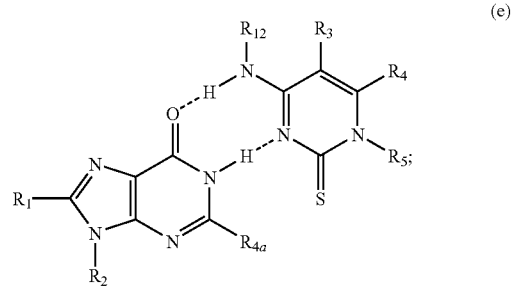

(e)

-continued
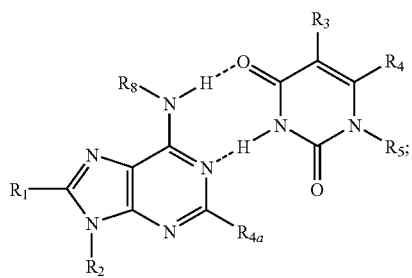 (f)
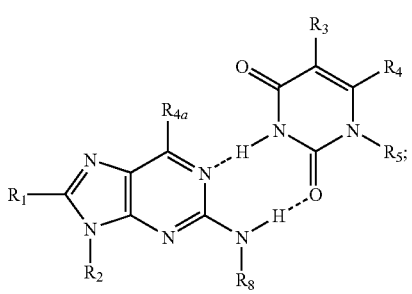 (g)
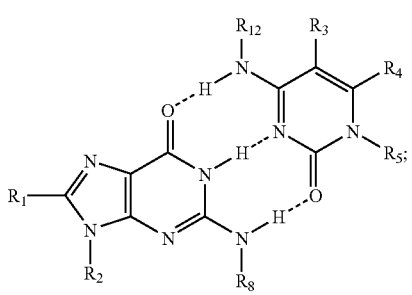 (h)
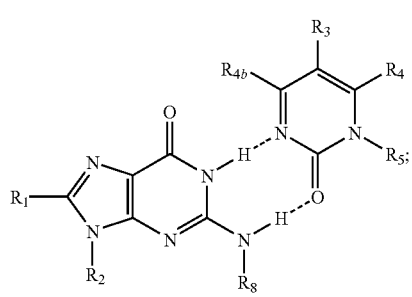 (i)
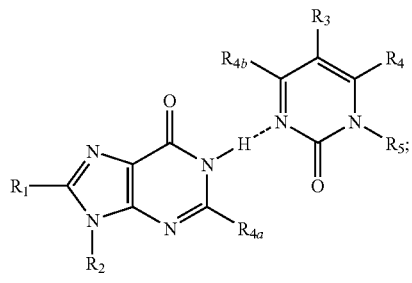 (j)
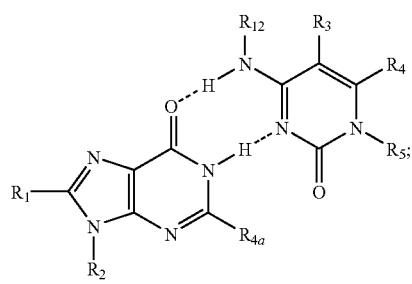 (k)
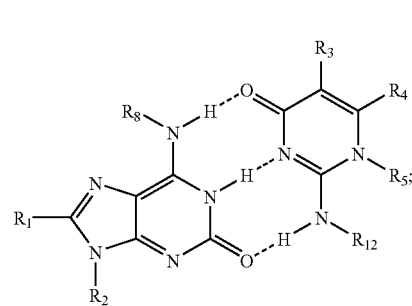 (l)
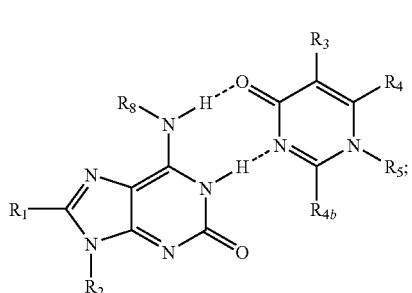 (m)
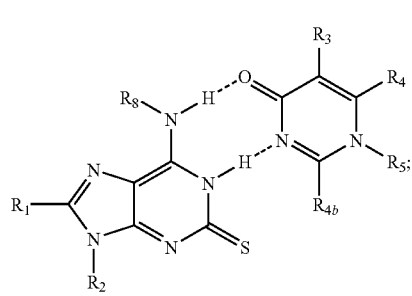 (n)
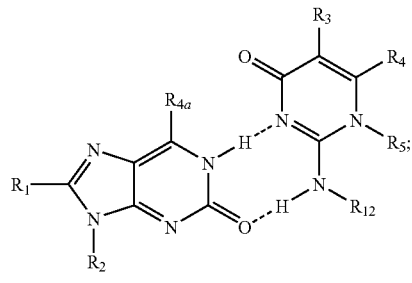 (o)

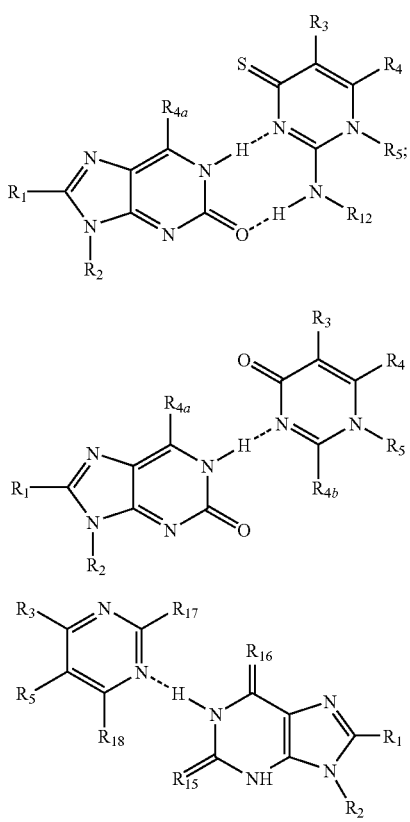

Examples of the pairing of certain base pairs of the invention is shown in the following tables. The number of indicated hydrogen bonds is also given.

TABLE A

| Base Pairs | formula (10) | formula (1) |
|---|---|---|
| formula (7) | 3 H-bonds | 2 H-bonds |
| formula (8) | repulsion | 2 H-bonds |

TABLE B

| Base Pairs | formula (10) | formula (2) |
|---|---|---|
| formula (7) | 3 H-bonds | 2 H-bonds |
| formula (9) | repulsion | 2 H-bonds |

TABLE C

| Base Pairs | formula (3) | formula (11) |
|---|---|---|
| formula (5) | 3 H-bonds | 2 H-bonds |
| formula (6) | repulsion | 2 H-bonds |

TABLE D

| Base Pairs | formula (3) | formula (4) |
|---|---|---|
| formula (5) | 3 H-bonds | repulsion |
| formula (12) | 2 H-bonds | 2 H-bonds |

TABLE E

| Base Pairs | formula (13) | formula (15) |
|---|---|---|
| formula (16) | 3 H-bonds | 2 H-bonds |
| formula (17) | repulsion | 2 H-bonds |

TABLE F

| Base Pairs | formula (13) | formula (14) |
|---|---|---|
| formula (16) | 3 H-bonds | repulsion |
| formula (18) | 2 H-bonds | 2 H-bonds |

In one embodiment, a pair of molecular entities comprises the three hydrogen bond base pair IsoCytosine and isoGuanine. For example, the following are 2 hydrogen base pairs:
4-oxo-pyrimidine and isoGuanine
4-oxo-pyrimidine and isoThioGuanine
isoCytosine and 2-oxo-purine
isoThioCytosine and 2-oxo-purine
and the one hydrogen bond pair 4-oxo-purine and 2-oxo-purine. See FIG. 2.

In another embodiment, a pair of molecular entities comprises the three hydrogen bond base pair 1,4-diaminopyrimidine-5-yl and Xanthine. Xanthine also may form two hydrogen bond base pairs with 1-diaminopyrimidine-5-yl or with 4-diaminopyrimidine-5-yl. In each of those pairings, one of the two amino groups from 1,4-diaminopyrimidine-5-yl is removed. See FIG. 7, left side pairings. In yet another embodiment, 1 or 4-diaminopyrimidine-5-yl can form a two hydrogen bond base pair with a Xanthine derivative in which one of the two carbonyl oxygens is replaced by sulfur: 2-thioXanthine (X2s) or 6-thioXanthine (X6s). Mixing and matching these sorts of base pairings allows one to create a strand that is capable of hybridizing to more than one sequence on an opposite strand, thus allowing degeneracy in the binding of molecular entities carrying the different strands.

In one embodiment, the base pairs do not formally pair with any of the naturally occurring bases. In a further embodiment, the bases of the invention are used with the natural bases only, for example a single pair being sufficient to provide no DNA affinity and increased diversity.

Non-Natural Bases Comprising Halogen and Alkyl Groups

Other purine and pyrimidine-like molecules can also be used to vary affinity. For example, the number of hydrogen bonds may be varied by substituting the H for a halogen. In one embodiment, the bases of the invention are halogen-comprising non-natural bases, for example,
4-fluoro-2-oxo-pyrimidine (4-Ha-P)
2-fluoro-Adenine (2-Ha-A)
6-fluoro-isoAdenine (6-Ha-isoA)
6-fluoro-Inosine (6-Ha-I)
Examples of base pairs include two hydrogen bonds
4-Ha-P:G
4-Ha-P:Gs
2-Ha-A:U
2-Ha-A:U 2s
6-Ha-isoA:U
6-Ha-isoA:U4s
6-Ha-I:C
6-Ha-I:Cs and one hydrogen bond pairs 4-Ha-P:I
4-Ha-P:6-Ha-I
P:6-Ha-I
4-Ha-P:6-Ha-I.

For example, fluorine and chlorine are quite small substituents that may have a relatively small steric effect on base pairing, i.e. 2-fluoroAdenine will pair with both uracil and 2-thioUracil, essentially acting like an analogue of Adenine. Sterically smaller alternatives, such as fluorine and chlorine, to an amino group can be used that face both a carbonyl and a thiocarbonyl. In one embodiment, larger halogens such as Iodine may be used to affect binding patterns, i.e. 2-Iodo-Adenine may pair with Uracil, but not with 2-thio-Uracil.

In another embodiment, 6-bromo-Adenine could pair with uracil via two hydrogen bond, such as A:U. Moreover, the binding to 2-thioUracil may be further enhanced by a favorable hydrophobic interactions between the bromine and the thiocarbonyl creating a pair of triple hydrogen bond strength similar to D:U.

In one embodiment, the bases of the invention are methyl analogues, i.e. Me for Ha or H. For example, 2-methyl-Adenine may be used as an Adenine analogue with PNAs. While it will strongly repel 2-thioUracil, it may bind to Uracil with significantly reduced affinity relative to Adenine.

In one embodiment, the above mentioned derivatives have hydrogen/halogen or an amino group in a potentially Watson-Crick like base pairing position facing either a carbonyl or thiocarbonyl on the "partner" base, i.e., the pattern determining the base pairing. Any other substitutions however is also possible, that does not directly influence the Watson-Crick like base pairing rules.

Non-limiting examples include: Pyrimidines substituted in the 5-position; i.e. bromouracil; analogues of C with one 4-N substituent, i.e. 4-N-alkyl and 4-N-acyl derivatives of C/C2s; purines halogenated in the 8-position, i.e 8-bromo-Adenine and 9-deaza and/or 8-aza purine derivatives; 2 and 6-amino "purines" with small N-substituents, i.e. N-6-Acetyl-diaminopurine, N-6-Methyl-Guanine, and N-Methyl-Adenine.

In one embodiment of the invention, the molecular entities have PNA backbones and are (PNA) oligomers.

Diversity of Base Pairs

One of skill in the art will appreciate that the increased number of bases will provide an increased degeneracy over natural bases. In one embodiment, the degeneracy minimizes secondary and tertiary structure. The degeneracy also may provide the advantage of one probe that can be used to recognize more than one target exclusively.

As described above, because of the increased diversity, within the same reading frame the system allows multiple different PNAs to be recognized with the same affinity by one other PNA complementary to all of the PNAs, yet also allow each PNA to be recognized with unique specificity by other complementary, yet different PNAs.

For example, using twelve bases, $12^{12} \sim 9 \times 10^{12}$ different 12'mers can be constructed. See FIG. 6, for example. These can be divided into 91 subgroups, according to the number of complementary 12'mers with which they pair, from 1 to half a million. On average, each 12'mer will pair with 1400 others, creating $10^{16}$ different base pair combinations.

Thus, the information system of the invention is expended relative to "linear" information systems such as binary strings, bar codes, or natural oligomers based on A, C, G, U and T. In the present invention, what is read not only depends on the encoding entity, such as an oligomer, but also on which of the numerous complementary PNAs are selected to "read" it, i.e., bind or not bind.

In one embodiment, the diversity of the system provides a degeneracy that limits cross reactivity. As one 12'mer will pair with 1400 others, for example, this limits the multiplexing capability of the system, i.e., only a limited number of pairs can work simultaneously and independently of each other with no cross reactivity. Triple vs. double vs. single hydrogen bonded base pairs are distinguished by different affinity.

In one embodiment, for example, deaminated bases are expected to pair with approximately the same affinity with either carbonyl or thiocarbonyl bases (A:U=A:U2s; Aiso: U=Aiso:U4s; I:C=I:Cs; P:G=P:Gs). A single hydrogen bond pair, such as I:P, would similarly be expected to be weaker than I:C. This again provides even more diversity since for example, I and P each form tow stable two hydrogen bond complexes thus I will bind stronger to C and Cs than to P and P will bind stronger to G and Gs than to I.

Thus, in one embodiment, for each large number of bases produced from a group of bases, many of the bases will be similar and provide a potential for cross hydridization. However, each pair of oligomers may also be quite unique with very different binding affinities.

The bases can thereby, for example, be used in a method to design a probe. Since, for example, each molecular entity such as a oligonucleotide made from a series of the bases of the invention, will bind to so many other molecular entities, a series of probes may be chosen or designed that differs slightly in the number of interactions, such as hydrogen bonds, that may be involved in the binding. Thus, for example, an oligonucleotide of 8 bases will have thousands of potential binding partners using the bases of the invention. Each of these may have slightly different strengths of interaction. Thus, one can chose a probe that is very sensitive to binding conditions, such as temperature, or design a series of probes that each bind at a slightly different temperature. The differences in temperature can be useful, in for example, immunohistochemistry in a system that can be varied by slight changes in temperature. The number of possible binding partners allows one to fine tune a binding partner for affinity, speed, temperature, low specific affinity for other probes or other compounds present in a sample and other uses.

A method of designing a probe may include a screening method where the thousands of possibilities for a certain length oligomer or numerous size oligomers are screened for the desired strength of hybridization and unique hybridization properties.

An entity may be chosen based on fast hybridization kinetics, combined with sufficient length to provide stability as links in supra molecular visualization and amplification systems and diagnostics.

For example, one may also use the system to design a series of probes or an information encoding system where each probe specifically hybridizes to a different target. One may further design a specific detection system, in which one probe hybridizes to a group of or all of the probes (FIG. 4). Such a system would be analogous to a hotel where each guest has a key unique to her own room, yet there is also a "master key" that will open every room.

The binding affinity between entities of base pairs may be a relative predictable function of length and triple, double, and single hydrogen bonded base pairs. The kinetic stability of the complexes once formed may follow a similar trend.

Figure 5:
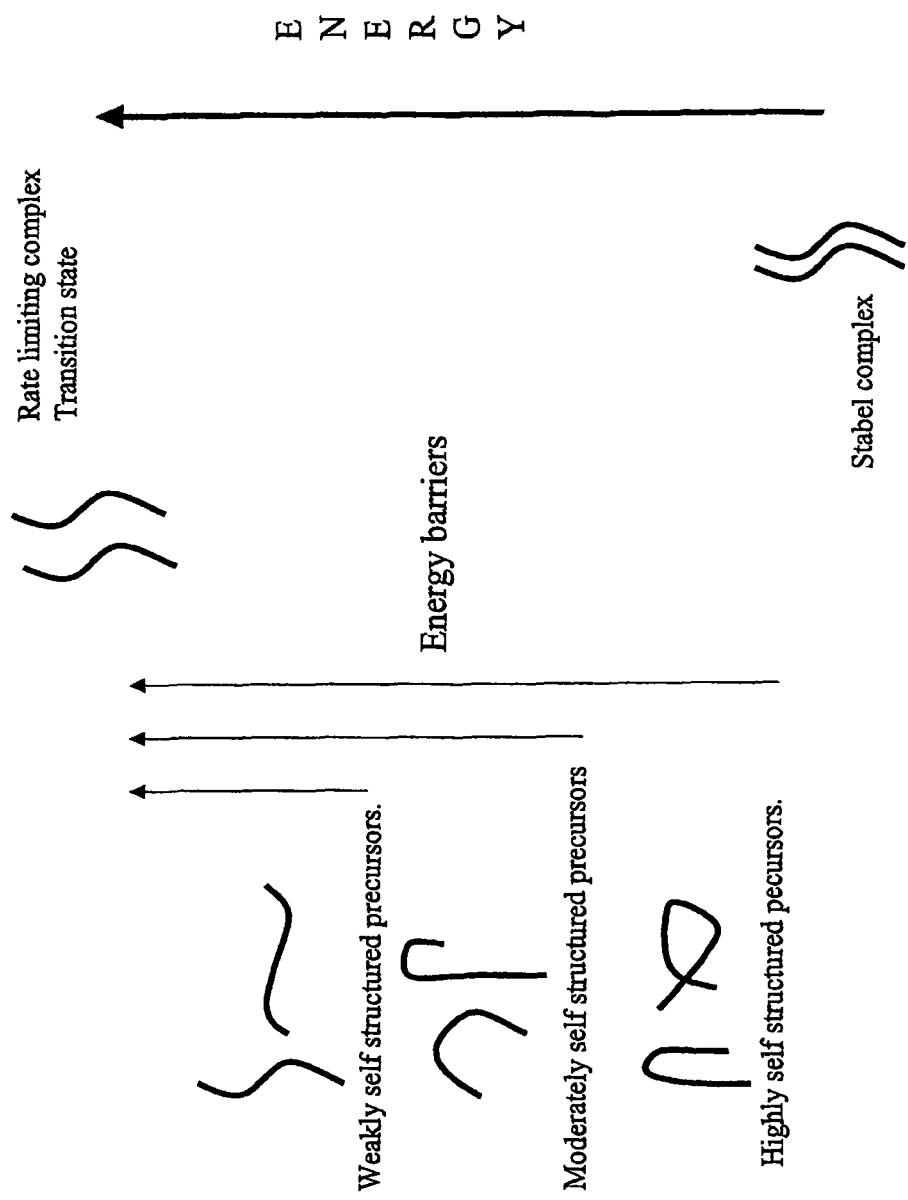
FIG. 5: Illustrates the difference in energy barrier to complex formation if the stable structures of the oligomers pre-complexation are aligned and/or by preparing oligomers that require little reorganization to reach the complexation transition state because of lack of a stable self structure (FIG. 5).

Binding affinity may be inversely proportional to the stability of the complex. For example, the longer and the more potential bond reach of an oligomer, the greater chance that it will be highly self structured and thus slow to hybridize. This can be expressed as a rate determining step preceding actual double-strand formation. More specifically, when two oligomers form a double-strand, the energy barrier to reaching the transition state will increase with the structure reorganization required of each of the hybridizing oligomers. Thus, one can reduce the energy barrier if the stable structures of the oligomers before hybridization are aligned and/or by preparing oligomers that require little reorganization to reach the transition state because of lack of a stable self structure (FIG. 5).

For example, intra molecular structure is a priori reduced by using more bases. For example, the 4 bases of DNA can form 16 pairs. Of these, 4 will be matches (25%) contributing on average with 2.5 hydrogen bonds. For example, 12 bases disclosed herein can form 144 pairs. Of these, only 22 will be matches (15%) and on average contribute with 2.1 hydrogen bonds. Since several consecutive base pairs are needed for stable intra molecular structures to form, this effect becomes quite pronounced. If it is assumed that 10 mutual hydrogen bonds are needed for a hair pin structure to form, and if 2×4 random DNA bases match, there is a 0.39% chance of hair pin formation. In contrast, using 12 bases instead of 4, there is only a 0.0084% chance of a hair pin because 2×5 bases must match for it to form. Adding more bases also aids in smart design of a probe because one may avoid aggregates or crystalline structures.

In one embodiment, the bases of the invention may be used to prepare molecular entities or oligomers with at least one of high binding affinity, variable binding affinity, rapid binding kinetics and absence of interference with RNA/DNA.

The degeneracy of the bases may also be utilized to design a molecular encoding system similar to the natural information encoding system of DNA but greatly enhanced because of the greater number of bases.

The bases of the invention may be used in any application in which natural bases, DNA, PNA, etc, are used.

Linkers

In addition to connecting a base to the backbone, a linker may also be used to connect at least one molecular entity to another or to bind a molecular entity to another composition. A person of ordinary skill in the art of molecular conjugation knows numerous linkers. Examples include 6-amino-hexanoic acid, succimidyl 4-(N-maleimidomethyl)cylohexane-1-carboxylate (SMCC), homobifunctional linkers such as glutaric dialdehyde, hexane di-isocyanate, dimethylapimidate, 1,5-difluoro-2,4-dinitrobenzene, divinyl sulfone (DVS), heterobifunctional linkers like e.g. N-gamma-maleimidobytyroloxy succinimide ester (GMBS), and zero length linkers such as 1-ethyl-3-(3-dimethylaminopropyl)carbodiimide Longer linker molecules based upon polyethylene glycol (PEG) are also available in the art. (See, for example, Discrete PEG (dPEG)™ modification reagents available from Quanta Biodesign, Ltd., Powell, Ohio, or at www.quantabiodesign.com; PEG-based reagents available from EMD Biosciences, Inc., San Diego, Calif., described in Novabiochem April, 2004, "Product focus: PEG reagents—bifunctional amino-PEG-acid spacers" brochure, available at www.novabiochem.com; and see Baumeister et al., *Biopolymers*, 71: 339 (2003); Kumar & Aldrich, *Org. Lett.*, 5: 613 (2003). (See also, "Chemistry of Protein Conjugation and Cross-Linking" Shan S. Wong CRC Press, Boca Raton, Fla., USA, 1993; "BioConjugate Techniques" Greg T. Hermanson Academic Press, San Diego, Calif., USA, 1996; "Catalog of Polyethylene Glycol and Derivatives for Advanced PEGylation, 2004" Nektar Therapeutics Inc, Huntsville, Ala., USA).

The present invention may also use a long uncharged linker comprising at least two units of the Formula I.

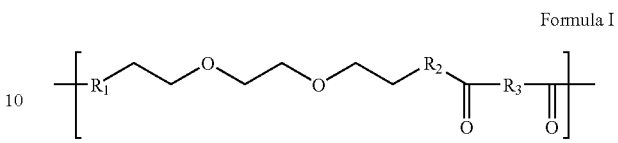

Formula I

In Formula I, R1 and R2 may comprise either NH or O, while R3 may comprise methyl, ethyl, propyl, CH2-O—CH2, and (CH2-O—CH2)2. For example, in some embodiments of the instant invention, the linker comprises at least two units of the Formula I wherein R1 and R2 are both NH and R3 is CH2-O—CH2. See the examples that follow and the accompanying International Application entitled "MONOMERIC AND POLYMERIC LINKERS USEFUL FOR CONJUGATING BIOLOGICAL MOLECULES AND OTHER SUBSTANCES" for further description of this linker.

Fluoresceins may also be added to the linkers. When fluoresceins are spaced apart by an L30 oligomer larger than L90 in an aqueous environment there may be negligible quenching. This contrasts with PEG-based spacers in aqueous solutions which may form a collapsed coiled structure.

For example, PNA probes with multiple fluorophores spaced via polymeric L30 may have higher water solubility, less aggregation and less non-specific binding, as compared to probes with just one fluorophore and no L30 spacer. Multiple PNAs joined together via L30 polymers may not aggregate and may have good solubility even with a total of 50-100 PNA bases in the same compound.

Detectable Labels

Compounds and compositions of the invention, including any molecular entity, may also include a detectable label which is any molecule which may be detected directly or indirectly so as to reveal the presence of a target in the sample. In some embodiments of the invention, a direct detectable label is used. Direct detectable labels may be detected per se without the need for additional molecules. Examples include fluorescent dyes, radioactive substances, and metal particles. In other embodiments of the invention, indirect detectable labels are used, which require the employment of one or more additional molecules. Examples include enzymes that affect a color change in a suitable substrate, as well as any molecule that may be specifically recognized by another substance carrying a label or react with a substance carrying a label. Other examples of indirect detectable labels thus include the non-natural bases of the present invention, antibodies, antigens, nucleic acids and nucleic acid analogs, ligands, substrates, and haptens.

Examples of detectable labels which may be used in the invention include fluorophores, chromophores, electrochemiluminescent labels, bioluminescent labels, polymers, polymer particles, bead or other solid surfaces, gold or other metal particles or heavy atoms, spin labels, radioisotopes, enzyme substrates, haptens, antigens, Quantum Dots, aminohexyl, pyrene, nucleic acids or nucleic acid analogs, or proteins, such as receptors, peptide ligands or substrates, enzymes, and antibodies (including antibody fragments).

Some detectable labels according to this invention comprise "color labels," in which the target is detected by the presence of a color, or a change in color in the sample. Examples of "color labels" are chromophores, fluorophores, chemiluminescent compounds, electrochemiluminescent labels, bioluminescent labels, and enzymes that catalyze a color change in a substrate. In some embodiments, more than one type of color may be used, for instance, by attaching distinguishable color labels to a single detection unit or by using more than one detection unit, each carrying a different and distinguishable color label.

"Fluorophores" as described herein are molecules that emit detectable electro-magnetic radiation upon excitation with electro-magnetic radiation at one or more wavelengths. A large variety of fluorophores are known in the art and are developed by chemists for use as detectable molecular labels and can be conjugated to the linkers of the present invention. Examples include fluorescein or its derivatives, such as fluorescein-5-isothiocyanate (FITC), 5-(and 6)-carboxyfluorescein, 5- or 6-carboxyfluorescein, 6-(fluorescein)-5-(and 6)-carboxamido hexanoic acid, fluorescein isothiocyanate, rhodamine or its derivatives such as tetramethylrhodamine and tetramethylrhodamine-5-(and -6)-isothiocyanate (TRITC). Other example fluorophores that could be conjugated to the instant linkers include: coumarin dyes such as (diethyl-amino)coumarin or 7-amino-4-methylcoumarin-3-acetic acid, succinimidyl ester (AMCA); sulforhodamine 101 sulfonyl chloride (TexasRed™ or TexasRed™ sulfonyl chloride; 5-(and -6)-carboxyrhodamine 101, succinimidyl ester, also known as 5-(and -6)-carboxy-X-rhodamine, succinimidyl ester (CXR); lissamine or lissamine derivatives such as lissamine rhodamine B sulfonyl Chloride (LisR); 5-(and -6)-carboxyfluorescein, succinimidyl ester (CFI); fluorescein-5-isothiocyanate (FITC); 7-diethylaminocoumarin-3-carboxylic acid, succinimidyl ester (DECCA); 5-(and -6)-carboxytetramethylrhodamine, succinimidyl ester (CTMR); 7-hydroxycoumarin-3-carboxylic acid, succinimidyl ester (HCCA); 6←fluorescein-5-(and -6)-carboxamido!hexanoic acid (FCHA); N-(4,4-difluoro-5,7-dimethyl-4-bora-3a,4a-diaza-3-indacenepropionic acid, succinimidyl ester; also known as 5,7-dimethylBODIPY™ propionic acid, succinimidyl ester (DMBP); "activated fluorescein derivative" (FAP), available from Molecular Probes, Inc.; eosin-5-isothiocyanate (EITC); erythrosin-5-isothiocyanate (ErITC); and Cascade™ Blue acetylazide (CBAA) (the O-acetylazide derivative of 1-hydroxy-3,6,8 pyrenetrisulfonic acid). Yet other potential fluorophores useful in this invention include fluorescent proteins such as green fluorescent protein and its analogs or derivatives, fluorescent amino acids such as tyrosine and tryptophan and their analogs, fluorescent nucleosides, and other fluorescent molecules such as Cy2, Cy3, Cy 3.5, Cy5, Cy5.5, Cy 7, IR dyes, Dyomics dyes, phycoerythrine, Oregon green 488, pacific blue, rhodamine green, and Alexa dyes. Yet other examples of fluorescent labels which may be used in the invention include and conjugates of R-phycoerythrin or allophycoerythrin, inorganic fluorescent labels such as particles based on semiconductor material like coated CdSe nanocrystallites.

A number of the fluorophores above, as well as others, are available commercially, from companies such as Molecular Probes, Inc. (Eugene, Oreg.), Pierce Chemical Co. (Rockford, Ill.), or Sigma-Aldrich Co. (St. Louis, Mo.).

Examples of polymer particles labels which may be used in the invention include micro particles, beads, or latex particles of polystyrene, PMMA or silica, which can be embedded with fluorescent dyes, or polymer micelles or capsules which contain dyes, enzymes or substrates.

Examples of metal particles which may be used in the invention include gold particles and coated gold particles, which can be converted by silver stains.

Examples of haptens that may be conjugated in some embodiments are fluorophores, myc, nitrotyrosine, biotin, avidin, strepavidin, 2,4-dinitrophenyl, digoxigenin, bromodeoxy uridine, sulfonate, acetylaminofluorene, mercury trintrophonol, and estradiol.

Examples of enzymes which may be used in the invention comprise horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase and glucose oxidase (GO).

Examples of commonly used substrates for horse radish peroxidase (HRP) include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), α-naphtol pyronin (α-NP), o-dianisidine (OD), 5-bromo-4-chloro-3-indolylphosphate (BCIP), Nitro blue tetrazolium (NBT), 2-(p-iodophenyl)-3-p-nitrophenyl-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B1-phosphate/fast red TR (NABP/FR), Naphthol-AS-MX-phosphate/fast red TR (NAMP/FR), Naphthol-AS-B1-phosphate/fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b(beta)-d (delta)-galactopyranoside (BCIG).

Examples of luminescent labels which may be used in the invention include luminol, isoluminol, acridinium esters, 1,2-dioxetanes and pyridopyridazines. Examples of electrochemiluminescent labels include ruthenium derivatives.

Examples of radioactive labels which may be used in the invention include radioactive isotopes of iodide, cobalt, selenium, hydrogen, carbon, sulfur and phosphorous.

In some embodiments the detection unit may comprise from 1 up to 500 detectable label molecules. In some embodiments, the detectable label is an enzyme, which may be conjugated to a polymer, such that the number of enzyme molecules conjugated to each polymer molecule is, for instance, 1 to 200, 2 to 50, or 2 to 25. In some embodiments, the detectable label is a gold particle, a radioactive isotope, or a color label, e.g. a low molecular weight fluorochrome, and the number of detectable labels conjugated to each polymer molecule is, for instance, 1 to 500, or for instance, 2 to 200. In some embodiments, the detectable label is a protein fluorochrome and the number of detectable labels conjugated to each polymer molecule is 1-50, 2-20. In some embodiments, the number of detectable label molecules conjugated to each polymer is 1-200, 2-50, 2-25, or is 10-20, 5-10, or 1-5. Add some more number ranges to pick from later on if necessary.

The detectable label can be detected by numerous methods, including, for example, reflectance, transmittance, light scatter, optical rotation, and fluorescence or combinations hereof in the case of optical labels or by film, scintillation counting, or phosphorimaging in the case of radioactive labels. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.). In some embodiments, more than one detectable label is employed.

When more than one color label is used, the different colors may have different, distinguishable colors. In some embodiments both colors can be detected simultaneously, such as by fusion or juxtaposition of the signals, signal enhancement or quenching, or detection of multiple colors in the sample. The exact choice of detectable label or combinations of detectable labels may be based on personal preferences in combinations with restrictions of the sample type, sample preparation method, detection method and equipment, and optional contrasting labels used in the sample.

Hybridization of Base Pairs

Two different base pairs or molecular entities may specifically hybridize. In some embodiments, the chosen hybridization conditions are "stringent conditions," meaning herein conditions for hybridization and washes under which nucleotide sequences that are significantly complementary to each other remain bound to each other. The conditions are such that sequences at least 70%, at least 80%, at least 85-90% complementary remain bound to each other. The percent complementary is determined as described in Altschul et al. (1997) Nucleic Acids Res. 25:3389-3402 (hereby incorporated by reference).

Specified conditions of stringency are known in the art and can be found in Current Protocols in Molecular Biology, John Wiley & Sons, Inc. (Ausubel et al. 1995 eds.), sections 2, 4, and 6 (hereby incorporated by reference). Additionally, specified stringent conditions are described in Sambrook et al. (1989) Molecular Cloning: A Laboratory Manual, 2nd ed. Cold Spring Harbor Press, chapters 7, 9, and 11 (hereby incorporated by reference).

In other embodiments, the chosen hybridization conditions are "high stringency conditions." An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In yet other embodiments, the chosen conditions are "moderately stringent conditions." Moderate stringency, as used herein, includes conditions that can be readily determined by those having ordinary skill in the art based on, for example, the length of the molecular entity or a specific nucleic acid pr nucleic acid analog segment. Exemplified conditions are set forth by Sambrook et al. Molecular Cloning: A Laboratory Manual, 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the chosen conditions are "low stringency" conditions. Low stringency conditions may include, as used herein, conditions that can be readily determined by those having ordinary skill in the art based on, for example, the length of the molecular entity. Low stringency may include, for example, pretreating the segment for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% W/V dextran sulfate, and 5-20×106 CPM probe is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

Polymers

The compounds and compositions of the invention, including any molecular entity may also comprise at least one polymer. A "polymer," as used herein, may be any molecule that facilitates covalent or non-covalent attachment of one or more other components or molecular entities. For instance, the polymer may facilitate the attachment of one or more probes, molecular entities, nucleic acid analog segments, and or detectable labels. The polymer may be a soluble molecule or an insoluble molecule and may have any shape including a linear polymer, branched polymer, bead or other globular shaped polymer.

Examples of suitable polymers include polysaccharides such as dextrans, carboxy methyl dextran, dextran polyaldehyde, carboxymethyl dextran lactone, and cyclodextrins; pullulans, schizophyllan, scleroglucan, xanthan, gellan, O-ethylamino guaran, chitins and chitosans such as 6-O-carboxymethyl chitin and N-carboxymethyl chitosan; derivatized cellulosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as ficoll and carboxymethylated ficoll; vinyl polymers including poly(acrylic acid), poly(acryl amides), poly(acrylic esters), poly(2-hydroxy ethyl methacrylate), poly(methyl methacrylate), poly(maleic acid), poly (maleic anhydride), poly(acrylamide), poly(ethyl-co-vinyl acetate), poly(methacrylic acid), poly(vinylalcohol), poly(vinyl alcohol-co-vinyl chloroacetate), aminated poly(vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs. Also contemplated is the use of mixed polymers, i.e., a polymer comprised of one or more of the above examples including any of the polymers, the co-block polymers and random co-polymers.

Properties of the polymer can be varied, depending on the desired application, to optimize performance. Examples of parameters that may be considered in the choice of a polymer include the length of the polymer and branching of the polymer. Furthermore, the polymer may carry various substituents. The substituents may be chemically protected and/or activated, allowing the polymer to be derivatized further. Give some relevant embodiments.

Kits

The invention also provides a kit comprising one or more compositions according to the invention. The kit may optionally comprise one or more binding agents, and suitable reagents for, for instance: antigen retrieval, sample dilution, reagent dilution, blocking of non-specific binding, blocking of endogenous enzyme activity, or blocking of repetitive sequences. The kit may optionally also comprise at least one container, instructions for use, and reference targets or samples.

EXAMPLES

Example 1a

Preparation of Pyrimidinone-Monomer

1. In dry equipment 4.6 g of solid Na in small pieces was added to 400 mL ethanol (99.9%), and was dissolved by stirring. Hydroxypyrimidine hydrochloride, 13.2 g, was added and the mixture refluxed for 10 minutes. Then 12.2 mL ethyl-bromoacetate (98%) was added and the mixture refluxed for 1½ hour. The reaction was followed using Thin Layer Chromatography (TLC). The ethanol was evaporated leaving a white compound, which was dissolved in a mixture of 80 mL of 1M NaCitrate (pH 4.5) and 40 mL of 2M NaOH. This solution was extracted four times with 100 mL Dichloromethane (DCM). The DCM phases were pooled and washed with 10 mL NaCitrate/NaOH-mixture. The washed DCM phases were evaporated under reduced pressure and resulted in 17.2 g of crude solid product. This crude solid product was recrystallized with ethylacetate giving a yellow powder. The yield for this step was 11.45 g (63%).

2. The yellow powder, 12.45 g. from above was hydrolyzed by refluxing overnight in a mixture of 36 mL DIPEA, 72 mL water and 72 mL dioxane. The solvent was evaporated and water was removed from the residue by evaporation from toluene. The yield for this step was 100%.

3. OBS. Pyrimidinone acetic acid (10.5 g), 16.8 g PNA-backbone ethylester, 12.3 g DHBT-OH, 19 mL Triethylamine was dissolved in 50 mL N,N-dimethylformamide (DMF). DIPIDIC (11.8 mL) was added and the mixture stirred overnight at room temperature. The product was taken up in 100 mL DCM and extracted three times with 100 mL of dilute aqueous $NaHCO_3$. The organic phase was extracted twice with a mixture of 80 mL of 1M NaCitrate and 20 mL of 4M HCl. Because TLC showed that some material was in the citrate phase, it was extracted twice with DCM. The organic phases were pooled and evaporated. Because there was a precipitation of urea, the product was dissolved in a DCM, and the urea filtered off. Subsequent evaporation left an orange oil. Purification of the orange oil was performed on a silica column with 10% methanol in DCM. The fractions were collected and evaporated giving a yellow foam. The yield for this step was 7.0 g (26.8%).

4. The yellow foam (8.0 g) was hydrolyzed by reflux overnight in 11 mL DIPEA, 22 mL water, and 22 mL dioxane. The solvent was evaporated and the oil was dehydrated by evaporation from toluene leaving an orange foam. The yield for this step was 100%.

Example 1b

Alternative Method of Preparing Pyrimidinone Monomer

Step 1. In dry equipment 9.2 g of solid Na in small pieces was dissolved in 400 mL ethanol (99.9%), with stirring. Hydroxypyrimidine hydrochlorid, 26.5 g, was added, and the mixture was stirred for 10 minutes at 50° C. Then 24.4 mL Ethyl bromoacetate (98%) was added and the mixture stirred at 50° C. for 1 hour. The reaction was followed using Thin Layer Chromatography (TLC).

The ethanol was evaporated leaving a white compound, which was dissolved in 70 mL of water and extracted with 20 mL DCM. Another 30 mL of water was added to the water phase, which was extracted with 3×100 mL DCM. The DCM-phase from the first extraction contains a lot of product, but also some impurities, wherefore this phase was extracted twice with water. These two water phases then were back extracted with DCM.

The combined DCM phases were pooled and washed with 10 mL water. The washed DCM phases were evaporation under reduced pressure and resulted in 25.1 g yellow powder. The yield for this step was 25.1 g=69%. Maldi-Tof: 181.7 (calc. 182).

Step 2. 34.86 g yellow powder from above was dissolved in 144 mL 2M NaOH. After stirring 10 minutes at room temperature, the mixture was cooled in an ice bath. Now 72 mL 4 M HCl (cold) was added. The product precipitated. After stirring for 5 minutes, the precipitate was filtered and thoroughly washed with ice water. Drying in a dessicator under reduced pressure left 18.98 g yellow powder. The yield for this step was 18.98 g=64%.

Step 3. Pyrimidinone acetic acid 11.1 g and triethylamine 12.5 mL were dissolved in N,N-dimethylformamide (DMF) 24 ml, HBTU 26.2 g was added plus 6 mL extra DMF. After 2 minutes a solution of PNA-Backbone ethylester 14.7 g dissolved in 15 mL DMF was added. The reaction mixture was stirred at room temperature and followed using TLC. After 1½ hour precipitate had formed. This was filtered off.

The product was taken up in 100 mL DCM and extracted with 2×100 mL dilute aqueous NaHCO3. Both of the aqueous phases were washed with a little DCM. The organic phases were pooled and evaporated. Evaporation left an orange oil. Purification of the product was done on a silica column with 10-20% methanol in ethylacetate. The fractions were collected and evaporated giving a yellow oil. The oil was dissolved and evaporated twice from ethanol. The yield from this step was 20.68 g=90%.

Step 4. The yellow oil (18.75 g) was dissolved in 368 mL 0.2 M $Ba(OH)_2$. Stirring for 10 minutes before 333 mL 0.221 M H2SO4 was added. A precipitation was performed immediately. Filtration through cellite, which was washed with water. The solvent was evaporated. Before the evaporation was at end, the product was centrifuged to get rid of the very rest of the precipitation. Re-evaporation of the solvent left a yellow oil. The yield from this step was 13.56 g=78%.

Step 5. To make a test on the P-monomer 3 consecutive P's were coupled to Boc-L300-Lys(Fmoc)-resin, following normal PNA standard procedure. The product was cleaved from the resin and precipitated also following standard procedures: HPPP-L300-Lys(Fmoc). Maldi-T of on the crude product: 6000 (calc. 6000) showing only minor impurities.

Example 2

Preparation of Thio-Guanine Monomer 1. 6-Chloroguanine (4.93 g) and 10.05 g $K_2CO_3$ was stirred with 40 mL DMF for 10 minutes at room temperature. The reaction mixture was placed in a water bath at room temperature and 3.55 mL ethyl bromoacetate was added. The mixture was stirred in a water bath until TLC (20% Methanol/DCM) showed that the reaction was finished. The precipitated carbonate was filtered off and washed twice with 10 mL DMF. The solution, which was a little cloudy, was added to 300 ml water, whereby it became clear. On an ice bath the target compound slowly precipitated. After filtration the crystals were washed with cold ethanol and dried in a desiccator. The yield for this step was 3.3 g (44.3%) of ethyl chloroguanine acetate.

2. Ethyl chloroguanine acetate (3.3 g) was dissolved by reflux in 50 mL absolute ethanol. Thiourea (1.08 g) was added. After a refluxing for a short time, precipitate slowly began forming. According to TLC (20% Methanol/DCM) the reaction was finished in 45 minutes. Upon completion, the mixture was cooled on an ice bath. The precipitate was then filtered and dried overnight in a desiccator. The yield for this step was 2.0 g (60%) ethyl thioguanine acetate.

3. Ethyl thioguanine acetate (3.57 g) was dissolved in 42 mL DMF. Benzylbromide (2.46 mL) was then added and the mixture stirred in an oil bath at 45° C. The reaction was followed using TLC (25% Methanol/DCM). After 3 hours all basis material was consumed. The step 3 target compound precipitated upon evaporation under reduced pressure and high temperature. The precipitate was recrystallized in absolute ethanol, filtered and then dried in a desiccator. The yield for this step was 3.88 g (82%) of methyl benzyl thioguanine ethylester.

4. Methyl benzyl thioguanine ethylester (5.68 g) was dissolved in 12.4 mL of 2M NaOH and 40 mL THF, and then stirred for 10 minutes. The THF was evaporated by. This was repeated. The material was dissolved in water and then 6.2 mL of 4M HCl was added, whereby the target product precipitated. Filtering and drying in a desiccator. The yield for this step was 4.02 g (77%).

5. The product of step 4 (4.02 g), 3.45 g backbone ethylester, 9 mL DMF, 3 mL pyridine, 2.1 mL triethylamine and 7.28 g PyBop were mixed and then stirred at room temperature. After 90 minutes a solid precipitation formed. The product was taken up in 125 mL DCM and 25 mL methanol. This solution was then extracted, first with a mixture of 80 mL of 1M NaCitrate and 20 mL of 4M HCl, and then with 100 mL dilute aqueous $NaHCO_3$. Evaporation of the organic phase gave a solid material. The material was dissolved in 175 mL boiling ethanol. The volume of the solution was reduced to about 100 mL by boiling. Upon cooling in an ice bath, the target product precipitate. The crystals were filtered, washed with cold ethanol and then dried in a desiccator. The yield of this step was 6.0 g (86%.)

6. The product of step 5 (6.0 g) was dissolved in 80 mL THF, 7.5 mL 2M NaOH and 25 mL water. The solution became clear after ten minutes of stirring. THF was evaporated. Water (50 mL) was added to the mixture. THF was evaporated. Water (50 mL) was added to the mixture. When the pH was adjusted by the addition of 3.75 mL of 4M HCl, thio-guanine monomer precipitated. It was then filtered, washed with water and dried in a desiccator. The yield for this step was 5.15 g (91%).

Example 3

Preparation of Diaminopurine Acetic Acid Ethyl Ester

1. Diaminopurine (10 g) and 40 g of $K_2CO_3$ were added to 85 mL of DMF and stirred for 30 minutes. The mixture was cooled in a water bath to 15° C. Ethyl bromoacetate (3 mL) was added three times with 20 minute intervals between each addition. This mixture was then stirred for 20 minutes at 15° C. The mixture was left in the water bath for another 75 minutes, and the temperature increased to 18° C. The DMF was removed by filtering and the remaining $K_2CO_3$ was added to 100 mL of ethanol and refluxed for 5 minutes. Filtering and repeated reflux of the $K_2CO_3$ in 50 mL ethanol, filtering. The pooled ethanol phases were placed in a freezer, after which crystals formed. These crystals were filtered, washed with cold ethanol, filtered again and then dried in a desiccator overnight. The yield for this step was 12 g (76%).

Example 4

Preparation of $L_{30}$-Linker

1. A solution of 146 mL of 2,2'-(Ethylenedioxy)bis(ethylamine) (98%) in 360 mL of THF was cooled in an ice bath. Di-tert-butyl dicarbonate (97%) (65 g) in 260 mL THF was added dropwise over one hour. The solvent was evaporated. The remaining oil was dissolved in water and then evaporated off. The oily product was dissolved in 300 mL water, extracted with 300 mL DCM, then washed twice with 150 mL of DCM. The collected organic phase was washed with 50 mL of water before evaporating to about half the volume. The organic phase was then extracted with 400 mL of 1M NaCitrate (pH 4.5), and then extracted again with 50 mL of 1M NaCitrate (pH 4.5). The aqueous phases were washed with 50 mL DCM before cooling on an ice bath. While stirring, 100 mL of 10M NaOH was added to the aqueous washed aqueous phases resulting in pH of 13-14. In a separation funnel the product separated on its own. It was shaken with 300 mL DCM and 50 ml water. The organic phase was evaporated, yielding a white oil. The yield for this step was 48.9 g (65.7%). The product had a predicted molecular formula of $C_{11}H_{24}N_2O_4$ (MW 248.3).

2. Boc-amine (76.2 g) was dissolved in 155 mL pyridine. Diglycolic anhydride (54.0 g) (90%) was added. After stirring for 15 minutes the intermediate product separated out and then 117 mL Acetic Anhydride (min. 98%) was added and the mixture stirred at 95° C. for 1 hour. The solution was then put under reduced pressure and evaporated. Water (117 mL) was added, and the mixture was then stirred for 15 minutes, after which 272 mL of water and 193 mL of DCM were added. The organic layer was extracted twice with 193 mL of 1M $Na_2CO_3$ and then twice with a mixture of 72 mL of 4M HCl and 289 mL of 1M NaCitrate. After each extraction the aqueous phase was washed with a little DCM. The collected organic phase was washed with 150 mL of water. The solvent was evaporated leaving the product as an orange oil. This yield for this step was 100.3 g (0.29 mol) (94%). The product had a predicted molecular formula of $C_{15}H_{26}N_2O_7$ (MW 346.4).

3. The product from step 2 (100.3 g) was dissolved in an equal amount of THF and was then added dropwise to 169.4 mL of 2,2'-(Ethylenedioxy)bis(ethylamine) at 60° C. over the period of 1 hour. The amine was distilled from the reaction mixture at 75-80° C. and a pressure of $3 \times 10^{-1}$ mBar. The residue from the distillation was taken up in a mixture of 88 mL of 4M HCl and 350 mL of 1M NaCitrate and then extracted three times with 175 mL of DCM. The aqueous phase was cooled in an ice bath and was cautiously added to 105 mL of 10M NaOH while stirring. In a separation funnel the product slowly separated from the solution. When separated 100 mL of water and 950 mL of DCM were added to the product. Stirring for some minutes before pouring to a separation funnel. The pH in the aqueous phase should be 14. The aqueous phase was extracted four times with 150 mL of DCM. The solvent was evaporated. The oily residue was dehydrated by evaporation from toluene, giving a yellow oil. The yield for this step was 115.48 g (81%). The product had a predicted molecular formula of $C_{21}H_{42}N_4O_9$ (MW 494.6).

4. The Boc-amine (115.48 g) from step 3 was dissolved in 115 mL of pyridine. Diglycolic anhydride (40.6 g) (90%) was added and the mixture stirred for 15 minutes, after which the intermediate product came out. Acetic Anhydride (97 mL) (min. 98%) was added and the mixture stirred at 95° C. for 1 hour. The mixture was then evaporated under reduced pressure. The mixture was then cooled and then 80 mL of water was added. This mixture was stirred for 15 minutes and then 200 mL of water and 150 mL of DCM were added. The organic layer was extracted twice with 150 mL of 1M $Na_2CO_3$ and then twice with a mixture of 53 mL of 4M HCl and 213 mL of 1M NaCitrate. After each extraction the aqueous phase was washed with a little DCM. The collected organic phase was washed with 150 mL of water. The solvent was evaporated. The oily residue was dehydrated by evaporation from toluene, giving a yellow oil. The yield for this step was 125 g (92%). The product had a predicted molecular formula of $C_{25}H_{44}N_4O_{12}$ (MW 592.6), with a mass spectrometry determined molecular weight of 492.5.

Further purifying of the product could be done on a silica column with a gradient from 5-10% methanol in DCM. The yield from the column purification was 69% and produced a white oil.

5. White oil (12.4 g) from step 4 was dissolved in a mixture of 12 mL water and 12 mL 1,4-Dioxane (99%) and was then heated to reflux. DIPEA (6 mL was added and refluxed for 30 minutes. This mixture was cooled and then evaporated. The oily residue was dehydrated by evaporation from toluene, giving a yellow oil. The product had a predicted molecular formula of $C_{25}H_{46}N_4O_{14}$ (MW 610.6).

Example 5

Exemplary Embodiments of PNA Sequences

All made by PNA standard procedures (see Example 18)

TABLE 1

| Sequence designation | PNA sequences[1] | N-terminal | C-terminal | Molecular Weight |
|---|---|---|---|---|
| Seq. AA | TCD-DG$_s$G$_s$-TAC-A | Flu-L$_{30}$- | -Lys(Cys) | 8805 |
| Seq. AB | U$_s$GU$_s$-DPP-TTG-D | Flu-L$_{30}$- | -Lys(Cys) | 8727 |
| Seq. AC | CU$_s$G$_s$-G$_s$DD-TU$_s$D-G$_s$DC | Flu-L$_{30}$- | -Lys(Cys) | 9413 |
| Seq. AD | GTP-TAA-TTP-PAG | Flu-L$_{30}$- | -Lys(Cys) | 9203 |
| Seq. AE | DG$_s$T-CG$_s$D-DG$_s$G-U$_s$CU$_s$ | Flu-L$_{30}$- | -Lys(Cys) | 9413 |
| Seq. AF | AGA-CPT-TPG-APT | Flu-L$_{30}$- | -Lys(Cys) | 9187 |
| Seq. AG | TCD-DII-TAC-A | Flu-L$_{30}$- | -Lys(Cys) | 8742 |

[1]Flu is fluorescein; T is thiamine; C is cytosine; D is diaminopurine; G$_s$ is thioguanine; A is Adenine; U$_s$ is 2/4-thiouracil; G is guanine; P is pyrimidone; I is inosine.

Example 6

Three PNAs with the $L_{30}$ Linker with Different Amino Acids at the C-Terminal BA: Flu-L$_{30}$-DGT-DTC-GTD-CCG-Lys(Acetyl)

BB: Flu-L$_{30}$-DGT-DTC-GTD-CCG-Lys(Cys)

BC: Flu-L$_{30}$-DGT-DTC-GTD-CCG-Lys(Lys)$_3$

Example 7

Synthesis of Flu-L$_{90}$-Lys(Flu)-L$_{30}$-Lys(Cys)

Using procedure provided in Example 18a, an MBHA-resin was loaded with Boc-Lys(Dde)-OH. Using a peptide synthesizer, amino acids were coupled according to PNA solid phase procedure provided in Example 18d yielding Boc-L$_{90}$-Lys(Fmoc)-L$_{30}$-Lys(Dde). The Boc and Fmoc protections groups were removed and the amino groups marked with fluorescein using the procedure in Example 18e. Then, the Dde protection group was removed and 0.4 M cysteine was added according to the procedure in Example 18b. The PNA was cleaved from the resin, precipitated with ether and purified on HPLC according to Example 18d. The product was found to have a molecular weight of 3062 using MALDI-TOF mass spectrometry; the calculated molecular weight is 3061.

Example 8

Synthesis of a Conjugate Made from Sequence AA from Example 5, DexVS70, and Flu(10)

Dextran (with a molecular weight of 70 kDa) was activated with divinylsulfone to a degree of 92 reactive groups/dextran polymer; this product is designated DexVS70.

| | |
|---|---|
| 280 μL DexVS70 | 20 nmol |
| 66 μL Flu$_2$Cys | 160 nmol (prepared from Example 7) |
| 25 μL 0.8 M NaHCO$_3$ pH = 9.5 | |
| 29 μL H$_2$O | |

The above four compounds were mixed. The mixture was placed in a water bath at 30° C. for 16 hours. The mixture was added to 50 nmol of freeze-dried PNA (sequence AA from Example 5). The mixture was placed in a water bath at 30° C. for 30 minutes. The conjugating reaction was quenched with 50 μL of 500 mM cysteine for 30 minutes at 30° C. Purification of the product was performed using FPLC: column SUPERDEX®-200, buffer 10 mM Hepes 100 mM NaCl, method 7 bank 2, Loop 1 mL. Two fractions were collected: one with the product and one with the residue. The relative absorbance Flu$_2$ ($\epsilon_{500nm}$=146000 M$^{-1}$, $\epsilon_{260nm}$=43350 M$^{-1}$) and PNA ($\epsilon_{500nm}$=73000 M$^{-1}$, $\epsilon_{260nm}$=104000 M$^{-1}$) was used to calculate the average conjugation ratio of Flu$_2$, PNA, and DexVS70. The conjugation ratio of Flu$_2$ to DexVS70 was 9.4. The conjugation ratio of PNA (sequence AA) to DexVS70 was 1.2.

Example 9

Synthesis of HRP-DexVS70-Seq. AA

Using the procedure of Example 14, the conjugate HRP-DexVS70-Seq. AA was made. The ratio of HRP to DexVS70 is 12.2; the ratio of Seq. AA to Dex70 is 1.2.

Example 10

Synthesis of GaM-DexVS70-Seq. AB

The synthesis of GaM-DexVS70-Seq. AB was performed using the procedure in Example 16 with the following changes as indicated.

Dextran (molecular weight 70 kDa) is activated with divinylsulfone to a degree of 92 reactive groups/dextran polymer.

| | |
|---|---|
| 105.0 µL DexVS70 | 7.5 nmol |
| 57.0 µL Goat anti mouse Imuno globuline (GAM-Ig) | 15 nmol |
| 8.9 µL 4 M NaCl | |
| 10.6 µL 0.8 M NaHCO$_3$ (pH = 9.5) | |
| 144.5 µL H$_2$O | |

The above five components were mixed and placed in a water bath at 30° C. for 40 minutes. Two hundred and ninety µL were taken out of the mixture and added to 100 nmol of Seq. AB, which was previously dissolved in 80 µL of H$_2$O. Then, 20 µL of 0.8 M NaHCO$_3$ (pH 9.5) was added and the mixture placed in a water bath at 30° C. for 1 hour. Quenching was performed by adding 39 µL of 500 mM cysteine and letting the resultant mixture set for 30 minutes at 30° C.

Purification of the product on FPLC: column SUPERDEX®-200, buffer 10 mM Hepes 100 mM NaCl, method 7 bank 2, Loop 1 mL. Two fractions were collected: one with the product and one with the residue. Relative absorbance PNA(Flu) ($\epsilon_{500nm}$=73000 M$^{-1}$) and GAM ($\epsilon_{278nm}$=213000 M$^{-1}$) (correction factor for PNA at 278 nm is due to the specific PNA and is calculated: 278/500 nm) was used to calculate the average conjugation ratio of PNA, GAM and DexVS70. The ratio of PNA to DexVS70 was 5.3 and the ratio of GaM to DexVS70 was 0.8.

Example 11

Exemplary Embodiments of PNA1-DexVS-PNA2 Conjugates

TABLE 2

| Conjugate designation | ratio | PNA1 | PNA1 nmol | PNA1 to DexVS | PNA2 | PNA2 nmol | PNA2 to DexVS | DexVS |
|---|---|---|---|---|---|---|---|---|
| Conj. CA | 1:9 | Seq. AA | 12.5 | 1.02 | Seq. AD | 100 | 8.2 | DexVS70 |
| Conj. CB | 1:6 | Seq. AC | 40 | 1.5 | Seq. AB | 200 | 7.4 | DexVS70 |
| Conj. CC | 1:16 | Seq. AC | 13.3 | 0.84 | Seq. AB | 200 | 12.7 | DexVS150 |
| Conj. CD | 1:6 | Seq. AC | 40 | 2.3 | Seq. AB | 200 | 11.5 | DexVS150 |

All conjugates were made by standard conjugation procedures of Example 17.

Example 12

Synthesis of Anti-Human-BCL2-DexVS70-PNA

Dextran (molecular weight 70 kDa) was activated with divinylsulphone to a degree of 92 reactive groups/dextran polymer, and is designated DexVS70. The antibody Anti-Human-BCL2 is designated AHB.

| | |
|---|---|
| 105 µL DexVS70 | 7.5 nmol |
| 800 µL AHB conc. (2.9 g/L) | 15.1 nmol |
| 25 µL 4 M NaCl | |
| 32 µL 0.8 M NaHCO$_3$ (pH = 9.5) | |

The above four compounds were mixed and placed in a water bath at 30° C. for 65 minutes. From this mixture, 875 µL was taken out and added to the indicated number of nmol of PNA in the table below; before the addition the PNA had been dissolved in the µL of H$_2$O indicated in the table below. Then the number of µLs of 0.8 M NaHCO$_3$ (pH 9.5) was added according to the table below. The resulting mixture was placed in a water bath at 30° C. for 70 minutes. Quenching was performed by adding 6 mg of solid cysteine (0.05 M) to the mixture and letting it stand for 30 minutes at 30° C.

Purification of the product on FPLC: column SUPERDEX®-200, buffer 10 mM Hepes 100 mM NaCl, method 7 bank 2, Loop 1 mL. Two fractions were collected: one with the product and one with the residue. Relative absorbance PNA(Flu) ($\epsilon_{500nm}$=73000 M$^{-1}$) and AHB ($\epsilon_{278nm}$=213000 M$^{-1}$) (correction factor for PNA at 278 nm is due to the specific PNA and is calculated: 278/500 nm) was used to calculate the average conjugation ratio of PNA, AHB and DexVS70.

Conjugates with different ratios PNA are shown in the following table.

TABLE 3

| Conjugate designation | nmol of PNA added | µL of H$_2$O added | µL of 0.8 M NaHCO$_3$ (pH 9.5) added | PNA to DexVS70 | AHB to DexVS70 |
|---|---|---|---|---|---|
| Conj. DA | 100 | 75 | 25 | 9.5 | 1.6 |
| Conj. DB | 33 | 30 | 10 | 2.9 | 1.2 |
| Conj. DC | 67 | 60 | 20 | 5.6 | 1.1 |

Example 13

Solid Phase Synthesis and Purification of Lys(Flu)-$L_{30}$-chr 17:14-$L_{30}$-Lys(Flu)-$L_{90}$-Lys(Flu)-$L_{90}$-Lys(Flu)

All Standard procedures are described in Example 18.

1. An MBHA-resin was loaded with Boc-$L_{30}$-Lys(Fmoc)-$L_{90}$-Lys(Fmoc)-$L_{90}$-Lys(Fmoc) using a standard loading procedure to a loading of 0.084 mmol/g.

2. To this resin, Boc-Lys(Fmoc)-$L_{30}$-AAC-GGG-ATA-ACT-GCA-CCT- was coupled using the peptide synthesizer machine following standard PNA solid phase chemistry. Fmoc protection groups were removed and the amino groups were labeled with fluorescein. After cleaving and precipitation the PNA was dissolved in TFA. The precipitate was washed with ether. The precipitate was dissolved in 200 μL NMP To this solution 6 mg Fmoc-Osu was added and dissolved. Next, DIPEA (9 μL) was added and the reaction was followed using MALDI-TOF mass spectrometry. After 30 minutes the reaction was finished and the PNA was precipitated and washed with ether.

HPLC after dissolving the PNA in 30% $CH_3CN$ and 10% $TFA/H_2O$ gave three pure fractions. The fractions were pooled and lyophilized. The lyophilized PNA was then dissolved in 192 μL NMP. Piperidine (4 μL) and 4 μL DBU was added to this solution which set for 30 minutes. Analysis by MALDI-TOF mass spectrometry gave a molecular weight of 10777.

The precipitate was washed with ether and was then dissolved in 100 μL TFA. The precipitate was washed with ether and then dried using $N_2$ gas.

Example 14

Standard Synthesis of HRP-DexVS70-PNA Conjugate

Dextran (molecular weight 70 kDa) is activated with divinylsulfone to a degree of 92 reactive groups/dextran polymer.

| 192 μL DexVS70 | 13.7 nmol |
| 255 μL horse radish peroxidase (HRP) | 602 nmol |
| 15 μL 4 M NaCl | |
| 19 μL 0.8 M $NaHCO_3$ pH = 9.5 | |
| 119 μL $H_2O$ | |

The above five components are mixed together placed in a water bath at 30° C. for 16 hours. Five hundred microliters of this mixture are added to 50 nmol PNA, which is previously dissolved in 40 μL $H_2O$. Then, 10 μL of 0.8 M $NaHCO_3$ (pH 9.5) is added. The mixture is then placed in a water bath at 30° C. for 2 hours. Quenching is performed by adding 55 μL of 110 mM cysteine and letting the resultant mixture set for 30 minutes at 30° C.

Purification of the product is performed by FPLC: column SUPERDEX®-200, buffer 10 mM Hepes 100 mM NaCl, method 7 bank 2, Loop 1 mL.

Two fractions are collected: one with the product and one with the residue. Relative absorbance HRP ($\epsilon_{404nm}$=83000 $M^{-1}$, $\epsilon_{500nm}$=9630 $M^{-1}$) and PNA(Flu) ($\epsilon_{500nm}$=73000 $M^{-1}$) is used to calculate the average conjugation ratio of HRP, PNA and DexVS70.

Example 15

Standard Synthesis of GAM-DexVS70-PNA Conjugate

Dextran (molecular weight 70 kDa) is activated with divinylsulfone to a degree of 92 reactive groups/dextran polymer (DexVS70).

| 105.0 μL DexVS70 | 7.5 nmol |
| 57.0 μL Goat anti mouse Imuno globuline (GAM) | 15 nmol |
| 8.9 μL 4 M NaCl | |
| 10.6 μL 0.8 M $NaHCO_3$ (pH = 9.5) | |
| 144.5 μL $H_2O$ | |

The above five components are mixed and placed in a water bath at 30° C. for 40 minutes. Two hundred and ninety μL is taken out of the mixture and added to 50 nmol of PNA, which is previously dissolved in 40 μL of $H_2O$. Then, 10 μL of 0.8 M $NaHCO_3$ (pH 9.5) is added and the mixture placed in a water bath at 30° C. for 1 hour. Quenching is performed by adding 34 μL of 500 mM cysteine and letting the resultant mixture set for 30 minutes at 30° C.

Purification of the product on FPLC: column SUPERDEX®-200, buffer 10 mM Hepes 100 mM NaCl, method 7 bank 2, Loop 1 mL. Two fractions are collected: one with the product and one with the residue. Relative absorbance PNA (Flu) ($\epsilon_{500nm}$=73000 $M^{-1}$) and GAM ($\epsilon_{278nm}$=213000 $M^{-1}$) (correction factor for PNA at 278 nm is due to the specific PNA and is calculated: 278/500 nm) was used to calculate the average conjugation ratio of PNA, GAM and DexVS70.

Example 16

Standard Synthesis of PNA1-DexVS70-PNA2

Dextran (molecular weight 70 kDa) is activated with divinylsulfone to a degree of 92 reactive groups/dextran polymer. PNA1 (100 nmol) is dissolved in 140 μL of DexVS70 (10 nmol). To this mixture 12.5 μL of PNA2 (12.5 nmol) dissolved in $H_2O$ is added, and then 30 μL of $NaHCO_3$ (pH 9.5) is added and the solution mixed. The resultant mixture is placed in a water bath at 30° C. for 35 minutes. Quenching was performed by adding 18.3 μL of 500 mM cysteine in Hepes and letting this mixture set for 30 minutes at 30° C.

Purification of the product on FPLC: column SUPERDEX®-200, buffer 10 mM Hepes 100 mM NaCl, method 7 bank 2, Loop 1 mL. Two fractions are collected: one with the product and one with the residue. Relative absorbance PNA (Flu) ($\epsilon_{500nm}$=73000 $M^{-1}$) and the proportion between the two PNA's is used to calculate the average conjugation ratio of PNA, PNA and DexVS70.

Example 17

Synthesis of the Boc-PNA-I(O-Bz)-Monomer

6-Benzyloxypurine

Sodiumhydride (60% Dispersion in mineral oil; 3.23 g; 80 mmol) was slowly added to benzyl alcohol (30 ml; 34.7 mmol). After the addition of more benzyl alcohol (10 ml) and 6-chloropurine (5.36 g;). The reaction mixture was heated to 100° C. for 4 hours. When the reaction mixture has reached room temperature, water (1 ml) was slowly added. 6-Benzyloxypurine was precipitated by the addition of acetic acid (4.6 ml) and diethylether (550 ml). The precipitate was separated by filtration (11.72 g). Re-crystallization from ether gave (4.78 g; 65.4%). Melting point was 175-177° C. (litt. 170-172° C.) [Ramazaeva N., 1989 #473] 1H-NMR (DMSO-d6): 8.53 (1H, s); 8.39 (1H, s); 7.54-7.35 (5H, m); 5.62 (2H, s).

Methyl (6-(Benzyloxy)purin-9-yl)acetate

6-Benzyloxypurine (4.18 g; 18.5 mmol) was added to a suspension of potassium carbonate (3.1 g; 22.4 mmol) in DMF (100 ml). After 15 min., bromoacetic acid methyl ester (1.93 ml; 20.4 mmol) was added. The reaction was monitored by TLC in butanol:acetic acid:water 4:1:1. Upon completion, the reaction mixture was partitioned between water (600 ml) and ethyl acetate (600 ml). The organic phase was dried over magnesium sulfate and evaporated to a volume of ~10 ml and precipitated with pet. ether. The two products were separated by column chromatography using ethyl acetate as the solvent. The products were precipitated in pet. ether. Yield: 2.36 g (43%). Melting point: 111.5-115° C. UV λmax=250 nm (9-alkylated); λmax=260 nm (7-alkylated). 1H-NMR (DMSO-d6): 8.60 (1H, s); 8.43 (1H, s); 7.6-7.35 (5H, m); 5.69 (2H, s); 5.26 (2H, s); 3.75 (3H, s).

(6-(Benzyloxy)purin-9-yl)acetic acid

Methyl (6-(Benzyloxy)purin-9-yl)acetate (2.10 g; 7.0 mmol) was dissolved in methanol (70 ml) and 0.1 M NaOH (85 ml) is added. After 15 min. the pH of the reaction mixture was lowered by addition of 0.1 M HCl (~80 ml) to pH 3. The precipitate was separated from the mixture by filtration and washed with water and ether. Yield: 1.80 g (90.2%). 1H-NMR (DMSO-d6): 8.55 (1H, s); 8.37 (1H, s); 7.55-7.30 (5H, m); 5.64 (2H, s); 5.09 (2H, s).

N-((6-(Benzyloxy)purin-9-yl)acetyl)-N-(2-Boc-aminoethyl)glycine

Ethyl N-(2-Boc-aminoethyl)glycinate (0.285 g; 1.15 mmol), (6-(benzyloxy)purin-9-yl)acetic acid (0.284 g; 1.0 mmol) and 3-hydroxy-1,2,3 benzotriazin-4(3H)-one (0.180; 1.1 mmol) was dissolved in dichlormethane/dimethylformamide 1:1 (10 ml). After addition of dicyclohexylcarbodiimide (0.248 g; 1.2 mmol) the reaction was left over night. The precipitate was removed by filtration. The organic phase was extracted twice with saturated sodium bicarbonate, dried with magnesium sulfate and evaporated to a oil. Column purification on silica using dichloromethane with 0-5% methanol as elutant yields the monomer ester which was dissolved in methanol (10 ml). Then, 0.1 M NaOH (12 ml) was added. After 30 min the reaction was filtered and pH adjusted with saturated KHSO4/water (1:3) to 2.7. The water phase was extracted twice with ethyl acetate (2×100 ml). The combined organic phases were dried over magnesium sulfate and evaporated to a volume of 10 ml. Precipitation with pet. ether yielded the monomer (0.15 g; 31%). 1H-NMR (DMSO-d6): 8.51 (1H, s); 8.23 (1H, s); 7.6-7.3 (5H, m); 5.64 (2H, s); 5.31 (ma.) +5.13 (mi.) (2H, s); 4.23 (mi.) +3.98 (ma.) (2H, s); 3.55-3.00 (4H, m); 1.36 (9H, s).

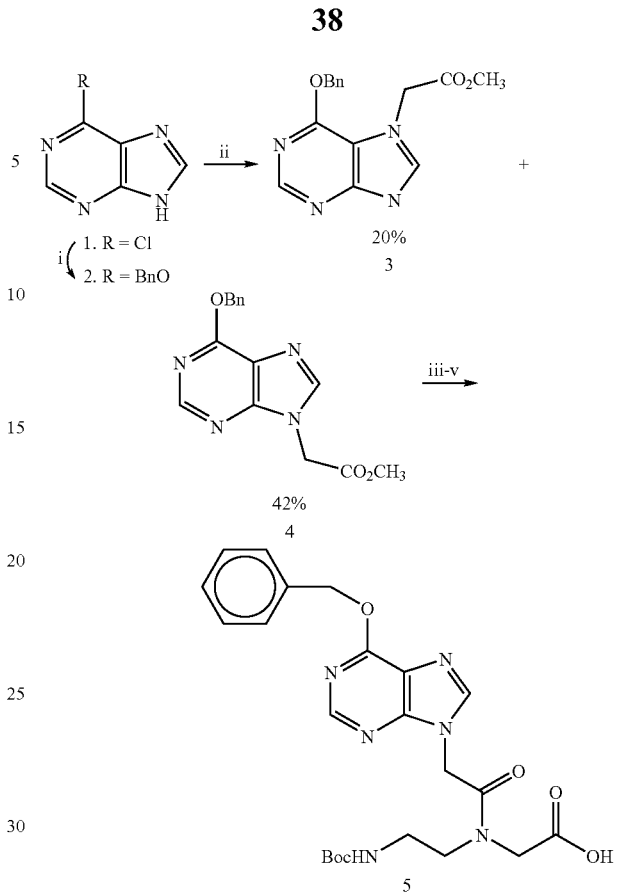

The synthesis of the hypoxanthine PNA monomer. (i) BnOH, NaH (ii) K2CO3, BrCH2CO2CH3 (iii) OH— (iv) DCC, Dhbt-OH, Boc-aeg-OEt (v) OH—

The Boc-PNA-Diaminopurine-(N6-Z)-monomer was prepared according to Gerald Haaima, Henrik F. Hansen, Leif Christensen, Otto Dahl and Peter E. Nielsen; Nucleic Acids Research, 1997, Vol 25, Issue 22 4639-4643.

The Boc-PNA-2-Thiouracil-(S-4-MeOBz)-monomer was prepared according to Jesper Lohse, Otto Dahl and Peter E. Nielsen; Proceedings of the National Academy of Science of the United States of America, 1999, Vol 96, Issue 21, 11804-11808.

The Boc-PNA-Adenine-(Z)-monomer was from PE Biosystems catalog GEN063011.

The Boc-PNA-Cytosine-(Z)-monomer was from PE Biosystems cat. GEN063013.

The Boc-PNA-Guanine-(Z)-monomer was from PE Biosystems cat. GEN063012.

The Boc-PNA-Thymine-monomer was from PE Biosystems cat. GEN063010.

IsoAdenine (2-aminopurine) may be prepared as a PNA-monomer by 9-N alkylation with methylbromoacetate, protection of the amino group with benzylchloroformate, hydrolysis of the methyl ester, carbodiimide mediate coupling to methyl-(2-Boc-aminoethyl)-glycinate, and finally hydrolysis of the methyl ester.

4-thiouracil may be prepared as a PNA-monomer by S-protection with 4-methoxy-benzylchloride, 1-N alkylation with methylbromoacetate, hydrolysis of the methyl ester, carbodiimide mediate coupling to methyl-(2-Boc-aminoethyl)-glycinate, and finally hydrolysis of the methyl ester.

Thiocytosine may be prepared as a PNA monomer by treating the Boc-PNA-cytosine(Z)-monomer methyl ester with Lawessons reagent, followed by hydrolysis of the methyl ester.

A number of halogenated bases are commercially available, and may be converted to PNA monomers analogously to the non-halogenated bases. These include the guanine analog 8-bromo-guanine, the adenine analogs 8-bromo-adenine and 2-fluoro-adenine, the isoadenine analog 2-amino-6-chloropurine, the 4-thiouracil analog 5-fluoro-4-thio-uracil, and the 2-thiouracil analog 5-chloro-2-thiouracil.

Boc-PNA-Uracil monomers were first described in "Uracil og 5-bromouracil I PNA," a bachelor project by Kristine Kilså Jensen, Københavns Universitet 1992.

Example 18

Miscellaneous Standard Procedures a. Loading of Resins.

P-methyl-BHA-resin (3 g) is loaded with Boc-Lys(Fmoc)-OH 15 mmol/g resin. The lysine is dissolved in NMP and activated with 0.95 equivalents (eq.) HATU and 2 eq. DIPEA. After loading the resin, it is capped by adding a solution of $(Ac)_2O/NMP/pyridine$ (at a ratio of 1/2/2) and letting it set for at least 1 hour or until Kaiser test was negative. After washing with DCM, the resin is dried in a dessicator. Quantitative Kaiser test typically gives a loading of 0.084 mmol/g.

b. Amino Acid Couplings.

The Boc protection group is removed from the resin with TFA/m-cresol (at a ratio of 95/5) 2×5 min. The resin is then washed with DCM, pyridine and DMF before coupling with the amino acid, which is dissolved in NMP in a concentration between 0.2 and 0.4 M and activated with 0.95 eq. of HATU and 2 eq of DIPEA for 2 minutes. The coupling is complete when the Kaiser test is negative. Capping occurring by exposing the resin for 3 minutes to $(Ac)_2O/pyridine/NMP$ (at a ratio of 1/2/2). The resin is then washed with DMF and DCM c. Boc-$L_{300}$-Lys(Fmoc)-Resin.

To the loaded Boc-Lys(Fmoc)-resin, $L_{30}$-Linker in a concentration of 0.26 M was coupled using standard amino acid coupling procedure. This was done 10 times giving Boc-$L_{300}$-Lys(Fmoc)-resin.

d. PNA Solid Phase.

On a peptide synthesizer (ABI 433A, Applied Biosystems) PNA monomers are coupled to the resin using standard procedures for amino acid coupling and standard PNA chemistry. Then the resin is handled in a glass vial to remove protections groups and to label with either other amino acids or fluorophores.

Removal of the indicated protection groups is achieved with the following conditions:

Boc: TFA/m-cresol (at a ratio of 95/5) 2×5 min.
Fmoc: 20% piperidine in DMF 2×5 min.
Dde: 3% hydrazine in DMF 2×5 min.

When the synthesis is finished, the PNA is cleaved from the resin with TFA/TFMSA/m-cresol/thioanisol (at a ratio of 6/2/1/1). The PNA is then precipitated with ether and purified on HPLC. MALDI-TOF mass spectrometry is used to determine the molecular weight of the product.

e. Labeling with Fluorescein.

5(6)-carboxy fluorescein is dissolved in NMP to a concentration of 0.2 M. Activation is performed with 0.9 eq. HATU and 1 eq. DIPEA for 2 min before coupling for at least 2×20 min or until the Kaiser test is negative.

Example 19

PNA with Positive and Negative Loadings

In order to make better conjugations at one time we tried to give the PNA a loading. Both PNA's were made by PNA standard procedures (See Example 18).

```
1. Flu-L30-Glu-TCA-AGG-TAC-A-Glu-L300-Lys(Cys)

Glu = glutamate has negative loadings and
for the easiness the PNA is designated -A4-

2. Flu-L30-Lys(Me)2-TGT-ACC-TTG-A-Lys(Me)2-
   L330-Lys(cys)

Lys(Me)2 = Boc-Lys(Me)2-OH has positive
loadings and the PNA is designated +T+
```

TABLE 4

| name | number | HRP | GaM | equiv. | HRP/Dex | GaM/Dex | PNA/Dex |
|---|---|---|---|---|---|---|---|
| -A4- | D13041 | D13050 | | 9 | 12.3 | | 0.13 |
| -A4- | D13041 | | D13060 | 7 | | 0.94 | 0.66 |
| +T4+ | D13042 | D13058 | | 9 | 13.5 | | 0.19 |
| +T4+ | D13042 | | D13056 | 7 | | 1.42 | 0.45 |

As it is shown in the scheme, PNAs with loading are not good at coupling.

Example 20

Target Detection: Procedures Used in the Examples Below

1. Fixation of Biological Samples

Tonsil tissue samples were fixed in neutral buffered formalin, NBF (10 mM $NaH_2PO_4/Na_2HPO_4$, pH 7.0), 145 mM NaCl, and 4% formaldehyde (all obtained from Merck, Whitehouse Station, N.J.). The samples were incubated overnight in a ventilated laboratory hood at room temperature.

2. Sample Dehydration and Paraffin Embedding

The tissue samples were placed in a marked plastic histocapsule (Sakura, Japan). Dehydration was performed by sequential incubation in 70% ethanol twice for 45 min, 96% ethanol twice for 45 min, 99% ethanol twice for 45 min, and xylene twice for 45 min. The samples were subsequently transferred to melted paraffin (melting point 56-58° C.) (Merck, Whitehouse Station, N.J.) and incubated overnight (12-16 hours) at 60° C. The paraffin-infiltrated samples were transferred to fresh warm paraffin and incubated for an additional 60 min prior to paraffin embedding in a cast (Sekura, Japan). The samples were cooled to form the final paraffin blocks. The marked paraffin blocks containing the embedded tissue samples were stored at room temperature in the dark.

3. Cutting, Mounting and Deparaffination of Embedded Samples

The paraffin blocks were cut and optionally also mounted in a microtome (0355 model RM2065, Feather S35 knives, set at 5.0 micrometer; Leica, Bannockburn, Ill.). The first few millimeters were cut and discarded. Paraffin sections 4-6 micrometers thick were then cut and collected at room temperature. The sections were gently stretched on a 45-60° C. hot water bath before being mounted onto marked microscope glass slides (SUPERFROST® Plus; Fisher, Medford, Mass.), two tissue sections per slide. The slides were then dried and baked in an oven at 60° C. The slides were deparaffinated by incubating twice in xylene for 5 min±2 min twice, then in 96% ethanol for 2 min+/−30 sec, then twice in 70% ethanol for 2 min+/−30 sec, and then once in Tris-buffered saline with TWEEN® (called herein TBST) for 5 min. TBST comprises 50 mM Tris adjusted to pH 7.6 with HCl; 150 mM NaCl; 0.05% TWEEN®20. The slides were deparaffinated by subsequently incubation in xylene twice for 5 min±2 min, 96% ethanol twice for 2 min+/−30 sec and 70% ethanol twice for 2 min+/−30 sec. The slides were immersed in deionized water and left for 1 to 5 min.

4. Endogenous Peroxidase Blocking

Samples were incubated with a 3% hydrogen peroxide solution for 5 min. to quench endogenous peroxidase activity, followed by washing in deionized water for 1 to 5 min.

5. Antigen Retrieval by Microwave Oven

Antigens in the sample were retrieved by immersing the slides in a container containing Antigen Retrieval Solution, pH 6.0 (DakoCytomation code No. K5204 Vial 7 or optional code No. K5205 Vial 7). The container was closed with a perforated lid and placed in the middle of a microwave oven and left boiling for 10 min. The container was removed from the oven and allowed to cool at room temperature for 20 min. The samples were rinsed in deionized water.

6. Antigen Retrieval by Water Bath Incubation

Antigens in the sample were retrieved by immersing the slides in a beaker containing Antigen Retrieval Solution, pH 6.0 (DakoCytomation code No. K5204 Vial 7 or optional code No. K5205 Vial 7). The samples were incubated for 40 min in a water bath at 95-100° C. The beaker was removed from the water bath and allowed to cool at room temperature for 20 min. The samples were rinsed in deionized water.

7. Water-Repellent Barrier to Liquids by DakoCytomation Pen

To ensure good coverage of reagent on the tissue sample, the area on the slide with tissue was encircled with a silicone rubber barrier using DakoCytomation Pen (DakoCytomation code No. 2002). The slides were transferred to a rack and placed in a beaker containing Tris-buffered saline with TWEEN® (called herein TBST) and left for 5 min. TBST comprises 50 mM Tris adjusted to pH 7.6 with HCl; 150 mM NaCl; 0.05% TWEEN®20.

8. Application of a Primary Antibody

Monoclonal Mouse anti-Human Cytokeratin (DakoCytomation code No. M3515) diluted 1:900 in ChemMate™ Antibody Diluent (DakoCytomation code No. S2022) was applied on the tissue samples and incubated for 30 min in a humid chamber at ambient temperature. The slides were individually rinsed and then washed in TBST for 5 min.

9. Application of Three Primary Antibodies

Monoclonal Mouse Anti-Human Cytokeratin (DakoCytomation code No. M3515) diluted 1:300, 1:900 and 1:1600; monoclonal Mouse Anti-Human CD20cy (DakoCytomation code No. M0755) diluted 1:2000, 1:8000 and 1:14000; and monoclonal Mouse Anti-Human Ki-67 Antigen (DakoCytomation code No. M7240) diluted 1:400, 1:1200 and 1:2400 were used. The antibodies were diluted in ChemMate™ Antibody Diluent (DakoCytomation code No. S2022), applied on the tissue samples, and incubated for 30 min in a humid chamber at ambient temperature. The slides were individually rinsed and washed in TBST for 5 min.

10. Application of an Antibody/Dextran/PNA1 Conjugate Recognition Unit

Antibody/Dextran/PNA1 conjugate recognition unit is also called "PNA1 conjugate" in the examples that follow.

The PNA1 conjugate comprises 70,000 molecular weight dextran. Table 1 summarizes PNA1 conjugates based on a secondary antibody: goat anti-mouse Ig, called herein GAM (DakoCytomation code No. Z0420). Table 2 summarizes PNA1 conjugates based on a primary antibody: mouse anti-human BCL2 oncoprotein, such as Clone 124 (DakoCytomation code No. M0887). The primary antibody was protein A-purified prior to conjugation. The conjugates were diluted in BBA (50 mM Tris adjusted to pH 7.6 with HCl; 150 mM NaCl; 2% BSA; 0.02% bronidox; 2.44 mM 4-aminoantipyrin) and were applied on the tissue sample in a range of dilutions, then incubated for 30 min in a humid chamber at ambient temperature. The slides were individually rinsed and washed in TBST for 5 min.

TABLE 5

PNA1 conjugates useful in indirect recognition of targets: GAM/Dextran/PNA1

| Conjugate No. | Sequence | µM Dex | GAM/Dex | PNA1/Dex |
|---|---|---|---|---|
| D14120 | AGA CPT TPG DPT | 1.25 | 1.1 | 4.3 |
| D14102 | GTP TAA TTP PAG | 1.02 | 1.0 | 9.1 |
| D14096 | GTP TAD TTP PAG | 1.15 | 1.4 | 4.2 |
| D14083 | $U_sGU_s$ DPP TTG D | 0.87 | 0.8 | 5.3 |
| D13171 | $U_sGU_s$ DPP TTG D | 1.21 | 1.0 | 7.5 |
| D13161 | TTG APP TTA G | 2.11 | 1.1 | 6.0 |
| D13150 | TGT APP TTGA | 2.20 | 1.1 | 4.2 |
| D13102 | TGT ACC TTGA | 2.53 | 1.1 | 2.5 |
| D12102 | TGT ACC TTGA | 2.50 | 1.3 | 4.5 |

TABLE 6

PNA1 conjugates for direct recognition of targets: anti-BCL2/Dextran/PNA1

| Conjugate No. | Sequence | µM Dex | Ab/Dex | PNA1/Dex |
|---|---|---|---|---|
| D14128 | $U_sGU_s$ DPP TTG D | 0.8 | 1.1 | 5.6 |
| D14126 | $U_sGU_s$ DPP TTG D | 1.0 | 1.2 | 2.9 |
| D14122 | $U_sGU_s$ DPP TTG D | 1.1 | 1.6 | 9.5 |

In the above tables, the letters A, C, G, U, and T, stand for the natural bases adenine, cytosine, guanine, uracil, and thymine. P stands for pyrimidinone, D for 2,6-diaminopurine, and $U_s$ for 2-thiouracil.

11. Fixation of PNA1-Conjugate with 1% Glutardialdehyde

The samples were washed in deionized water for 30 sec. Then, 1% glutardialdehyde (Merck Art. No. 820603), called herein GA, diluted in 22 mM calcium phosphate buffer, pH 7.2, was applied, and the samples were incubated for 10 min in a humid chamber at ambient temperature. The samples were washed in deionized water for 30 sec and in TBST for 5 min.

12. Application of a PNA$^1$-PNA$^2$/Dextran Conjugate Adaptor Unit

PNA$^1$-PNA$^2$/Dextran conjugate is also called "PNA$^1$-PNA$^2$" in the following examples. Table 7 summarizes the compositions of PNA$^1$-PNA$^2$ conjugates. PNA$^1$ is complementary to the PNA1 conjugate, and PNA$^2$ is complementary to the PNA2 conjugates D14079 and D13155 described in step 13 below. The sequence of PNA$^1$ is CU$_s$G$_s$ G$_s$DD TU$_s$D G$_s$DC and the sequence of PNA$^2$ is U$_s$GU$_s$ DPP TTG D, in which U$_s$ stands for 2-thio-uracil, G$_s$ stands for 2-amino-6-thioxopurine, D stands for diaminopurine, and P stands for pyrimidinone. The conjugates, diluted in BBA, were applied to the tissue samples in a range of dilutions, and the samples were then incubated for 30 min in a humid chamber at ambient temperature. The samples were individually rinsed and washed in TBST for 5 min. When testing a PNA$^1$-PNA$^2$ conjugate, fixed concentrations of 0.08 µM PNA1 and 0.05 µM PNA2 were used.

TABLE 7

PNA$^1$-PNA$^2$/Dextran conjugates

| Conjugate No. | Molecular weight of dextran | PNA$^1$/dex | PNA$^2$/dex | µM PNA$^1$ |
|---|---|---|---|---|
| D14119 | 150.000 | 2.3 | 11.5 | 4.2 |
| D14106 | 150.000 | 0.8 | 12.7 | 1.3 |
| D14104 | 70.000 | 1.5 | 7.5 | 3.9 |

13. Application of Horse Radish Peroxidase/Dextran/PNA2 Conjugate Detection Unit Horse Radish Peroxidase (HRP)/Dextran/PNA2 conjugates are also called "PNA2 conjugate" in the examples that follow, and are listed in table 8. The PNA2 conjugates comprise 70.000 Da molecular weight dextran. The conjugates diluted in BBA were applied to the tissue samples in a range of dilutions, and samples were incubated for 30 min in a humid chamber at ambient temperature. The samples were individually rinsed and washed twice in TBST for 5 min.

TABLE 8

PNA2 conjugates: HRP/Dextran/PNA2

| Conjugate No. | Sequence | µM PNA | HRP/Dex | PNA2/Dex |
|---|---|---|---|---|
| D14133 | TCD DII TAC A | 1.6 | 14.0 | 1.0 |
| D14114 | DG$_s$T CG$_s$D DG$_s$G U$_s$CU$_s$ | 3.9 | 11.4 | 2.1 |
| D14110 | DGT CG$_s$D DG$_s$G U$_s$CU$_s$ | 3.0 | 12.6 | 1.6 |
| D14089 | CU$_s$G$_s$ G$_s$DD TU$_s$D G$_s$DC | 2.1 | 14.1 | 1.5 |
| D14086 | U$_s$CG$_s$ G$_s$DD TU$_s$D GDC | 1.9 | 11.0 | 1.0 |
| D14079 | TCD DG$_s$G$_s$ TAC A | 1.9 | 12.2 | 1.2 |
| D13159 | CTA AG$_s$G$_s$ TCA A | 1.9 | 12.9 | 1.3 |
| D13155 | TCD DG$_s$G$_s$ TAC A | 2.4 | 12.7 | 1.6 |
| D13148 | TCA AG$_s$G$_s$ TAC A | 1.9 | 11.6 | 0.8 |
| D13122 | CTA AGG TCA A | 3.2 | 13.0 | 2.1 |
| D13108 | GTG TGT GT | 4.3 | 12.0 | 2.3 |
| D13106 | TCA AGG TAC A | 2.6 | 12.4 | 1.3 |
| D12120 | TCD DGG TAC A | 1.0 | 18.3 | 0.6 |
| D12094 | TCA AGG TAC A | 3.0 | 14.6 | 0.9 |

In Table 8, in addition to the nucleobase letter schemes provided for Tables 5-7, I stands for inosine.

14. Application of Diaminobenzidine Chromogenic Substrate Solution

The diaminobenzidine chromogenic substrate solution, DAB+ (DakoCytomation code No. K3468) was applied on the tissue samples, and the samples were incubated for 10 min in a humid chamber at ambient temperature. The samples were washed with deionized water for 5 min.

15. Counterstaining with Hematoxylin

The tissue samples were immersed in Mayers Hematoxylin (Bie & Berntsen Code No. LAB00254) for 3 min, rinsed in tap water for 5 min, and finally rinsed with deionized water.

16. Cover Slipping

Cover slips were applied to the tissue samples using the aqueous mounting media, Faramount (DakoCytomation code No. S3025).

17. Evaluation of the Performance

The tissue staining was examined in a bright field microscope at 10×, 20× or 40× magnification. Both the specific and the non-specific staining intensity were described with a score-system using the range 0 to 3+ with 0.5+ score interval. ChemMate™ EnVision™ Detection kit Rabbit/Mouse (DakoCytomation code No. K5007 bottle A) was used as a reference, and was included in all experiments for testing in parallel with the PNA conjugates. K5007 was used according to manufacturer's instructions. The antibodies were used in the following dilutions: M3515 at 1:900, M0755 at 1:8000, and M7240 at 1:1200. The staining intensity of the K5007 reference using the primary antibody M3515 diluted 1:900 was set to 2+ in order to compare and assess the staining result of the PNA conjugate tested. If the reference deviated more than ±0.5, the test was repeated.

In the examples, the various visualization system combinations of the invention were tested on routine tissue samples. The staining performance was compared with a reference visualization system, using EnVision™ and a very dilute antibody from DakoCytomation. The practical dynamic range of quantitative IHC may be narrow, and e.g. strongly stained (+3) tissues are not easy to compare with respect to intensity. Therefore, on purpose, the staining intensity of the reference system was adjusted to be approximately +2. This was done in order to better monitor and compare differences in staining intensity with the system of the invention.

Example 21

Protocol for Fast Evaluation of Non-Specific Binding of PNA2 Conjugates

The protocol allowed for a quick test of PNA2 conjugates for non-specific staining. Tonsil tissues were taken through the steps 1-5, 7, 13-14, 15 (in which the slides were immersed in a bath of Hematoxylin Mayer for 1 min.), and 16-17, above.

The conjugates to be tested were diluted to the final concentrations 0.05 µM and 0.2 µM. As references, two PNA2 conjugates were used in the final concentration 0.05 µM. The first reference, for example, PNA2, D13108, was known to give non-specific nuclear staining, and so was used as a positive control. The second reference, for example, PNA2, D13155, was known not to give any non-specific nuclear staining, and was used as a negative control. In general, 250 µL of each reagent was applied unless otherwise specified.

Protocol for Test of a PNA Pair with One Antibody

Tonsil tissues were taken through the steps 1-4, 6-8, 10, 11, and 13-17 above. Step 11 was left out for the tonsils not fixed with 1% GA. In general, 250 µL of each reagent was applied unless otherwise specified.

Protocol for Test of 3-Layer PNA Conjugates

Tonsil tissues were taken through the steps 1-4, 6-8, and 10-17 above. Step 11 was left out for the tonsils not fixed with 1% GA. In general, 250 µL of each reagent was applied unless otherwise specified.

Protocol for Test of a PNA Pair with 3 Antibodies

Tonsil tissues were taken through the steps 1-4, 6, 7, 9-11, and 13-17 above. Step 11 was left out for the tonsils not fixed with 1% GA. A further negative control, mouse IgG1 (DakoCytomation code No. X0931) diluted 1:300 in S2022 was included the protocol for the PNA conjugates. In general, 250 µL of each reagent was applied unless otherwise specified.

Example 22

Testing and Selection of PNA Pairs

Conjugates comprising example PNA segments were tested for their ability to specifically hybridize according to the invention. Tonsil tissues were taken through the steps 1-4, 6-8, 10 and 13-17 above. K5007 was included as a reference to secure the level of the staining. The concentration of the conjugates was 0.08 µM for PNA1 and 0.05 µM for PNA2.

The results listed in Table 10 show the staining intensities for a representative number of PNA pairs tested. The PNA pairs did not demonstrate any non-specific binding. The specific staining, in general, was directly proportional to the number of hydrogen bonds involved in the base-pairing. It was important that each PNA did not interact with itself. Substitution of T (thymine) with $U_s$ (2-thiouracil) in some PNAs could prevent such intra-PNA interactions. The unspecific staining intensity was increased by substituting an A with a D. On the other hand, we also observed that replacement of one G (guanine) with $G_s$ (2-amino-6-thioxopurine) in the same PNA could circumvent the unspecific binding introduced by D. For instance, the staining of the PNA1 conjugate D14102 was improved by substituting the D in D14096 with an A in D14102. As is apparent from Table 9, this small change resulted in an increase of the specific staining score by 1+.

TABLE 9

| PNA1 | PNA2 | Specific staining intensity | Non-specific staining intensity |
|---|---|---|---|
| D13161 | D13159 | 2 | 0 |
| D14083 | D14079 | 2.5 | 0 |
| D14096 | D14089 | 1.5 | 0 |
| D14102 | D14089 | 2.5 | 0 |
| D14120 | D14114 | 1.5 | 0 |

Example 23

The Effect of Base Substitution on PNA-Specific Binding Intensities

The PNA pair D13102-D13106 was used as a starting point for further investigation of introducing base substitutions in either PNA1 or PNA2 conjugates. Tonsil tissues were taken through the steps 1-4, 6-8, 10 and 13-17. Each of the three different PNA1 conjugates was tested with each of the three different PNA2 conjugates. The concentration of the conjugates used was 0.08 µM for PNA1 and 0.05 µM for PNA2.

TABLE 10

| | PNA2: | | |
|---|---|---|---|
| PNA1: | D13106 TCA AGG TAC A | D13148 TCA AG$_s$G$_s$ TAC A | D13155 TCD DG$_s$G$_s$ TAC A |
| D13102 TGT ACC TTG A | 2.5 | 0 | 2 |
| D13150 TGT APP TTG A | 2.5 | 0.5 | 3 |
| D13171 U$_s$GU$_s$ DPP TTGD | 3 | 2.5 | 3 |

Table 10 shows the effect of base substitutions on the specific binding between paired PNA variants. No non-specific binding was observed. D13102 tested with D13106 gave a specific staining of 2.5+. Replacement of 2 G's with 2 $G_s$'s (D13148) resulted in the abolishment of specific staining, but by introducing 2 D's instead of 2 A's (D13155) achieved a specific staining of 2+. When the 2 C's in D13102 were replaced with 2 P's (D13150) and tested with D13106, the specific staining was unchanged at 2.5+, despite the lower number of hydrogen bonds as compared to the PNA-pair D13102-D13106. Test of D13150 with D13148 resulted in a reduced specific staining of 0.5+, whereas specific staining to 3+ was observed for the D13150-D13155 pair. The replacement in D13150 of 2 A's with 2 D's and of 2 T's with 2 $U_s$'s (D13171) resulted in improved specific binding compared to D13106. This modified PNA1 was now able to bind specifically to D13148 with a score of 2.5+, and also bound to D13155.

This experiment clearly demonstrates the use of PNA pairs in the present invention. Furthermore, it shows the ability of fine tuning the specific binding by introducing base substitutions using either natural as well as non-natural bases.

Example 24

Test of Cross Reactivity

The two PNA-pairs, D13150-D13155 and D13161-D13159, were tested for cross-reactivity. Tonsil tissues were taken through the steps 1-4, 6-8, 10, and 13-17. The concentration of conjugates used was 0.16 µM for PNA1 and 0.1 µM for PNA2.

As apparent from Table 11, PNA1 D13150 did not cross react with PNA2 D13159, but PNA1 D13161 cross reacted with PNA2 D13155. We therefore excluded the PNA pair D13161-D13159 due to the cross-reaction between D13161 and D13155. No non-specific staining was observed.

TABLE 11

Test of specific binding and cross reactivity

| | PNA2: | |
|---|---|---|
| PNA1: | D13155 | D13159 |
| D13150 | 2.0 | 0 |
| D13161 | 1 | 1.5 |

Example 25

Test of Cross Reactivity

Three PNA-pairs, D14083-D14079, D14102-D14089 and D14120-D14114 were tested for cross-reactivity. Tonsil tissues were taken through the steps 1-4, 6-8, 10, and 13-17. The concentration of the conjugates used was 0.08 µM for PNA1 and 0.05 µM for PNA2.

The PNA conjugates listed in Table 12 only bound to their complementary partner and did not cross react to any of the other PNA conjugates tested. No non-specific staining was observed. See Table 12 below.

TABLE 12

Test of specific binding and cross reactivity

| | PNA2: | | |
|---|---|---|---|
| PNA1: | D14079 | D14089 | D14114 |
| D14083 | 1.5 | 0 | 0 |
| D14102 | 0 | 1 | 0 |
| D14120 | 0 | 0 | 1.5 |

Example 26

Two PNA pairs, D14083-D14079 and D14096-D14089, were tested at different PNA2 concentrations for the purpose of determining the optimal concentration of PNA2 conjugates. The concentrations used were 0.08 µM for PNA1 conjugates and 0.025; 0.05; 0.1 and 0.2 µM for PNA2 conjugates.

Tonsil tissues were taken through the steps 1-4, 6-8, 10, and 13-17. The optimal concentration of the PNA2 conjugate was 100 nM. See Table 13 below.

TABLE 13

Determination of PNA2 conjugate concentration.

| | 1% GA fixation | | Specific staining | | | |
|---|---|---|---|---|---|---|
| PNA1 | of PNA1 | PNA2 | 0.025 µM | 0.05 µM | 0.1 µM | 0.2 µM |
| D14083 | — | D14079 | 1.5 | 2 | 3 | 2.5 |
| D14096 | — | D14089 | 0.5 | 1 | 2 | 1.5 |

Tonsil tissues were taken through the steps 1-4, 6-8, 10, 11, and 13-17. Step 11 was omitted for tissues not fixed with 1% GA.

Fixation of PNA1 conjugates with 1% GA resulted in a stronger specific staining than without fixation and the optimal concentration of the PNA2 conjugate was now determined to be 50 nM. See Table 14 below.

TABLE 14

Effect of 1% GA fixation on the determination of PNA2 conjugate concentration.

| | 1% GA fixation | | Specific staining | | | |
|---|---|---|---|---|---|---|
| PNA1 | of PNA1 | PNA2 | 0.025 µM | 0.05 µM | 0.1 µM | 0.2 µM |
| D14083 | − | D14079 | 2 | 2 | 2.5 | 2.5 |
| D14083 | + | D14079 | 2.5 | 3 | 2.5 | 3 |

Example 27

Standard Synthesis of an Alkaline Phosphatase—Dextran—PNA Conjugate Molecule Alkaline Phosphatase ("AP") (from Calf Intestine, EIA grade) was dialyzed overnight against 2 mM HEPES, pH 7.2; 0.1M NaCl; 0.02 mM $ZnCl_2$. Dextran (molecular weight 70 kDa) was activated with divinylsulfone to a degree of 92 reactive groups per dextran polymer (DexVS70).

The three components below were mixed together and placed in a water bath at 40° C. for 30 minutes.

| 192.0 µL DexVS70 | 13.7 nmol |
|---|---|
| 41.0 µL PNA | 41 nmol PNA dissolved in $H_2O$ |
| 6.0 µL 1M $NaHCO_3$ | |

108.0 µL of the DexVS70-PNA conjugate was taken out and added to a mixture of:

| 160.0 µL AP | 43.4 nmol |
|---|---|
| 7.7 µL 1M $NaHCO_3$ | |
| 30.6 µL 20 mM Hepes, pH 7.2; 1M NaCl; 50 mM $MgCl_2$; 1 mM $ZnCl_2$ | |

The mixture was placed in a water bath at 40° C. for 3 hours. Quenching was performed by adding 30.6 µL of 0.1M ethanolamine and letting the mixture stand for 30 minutes in water bath at 40° C. The product was purified on FPLC with: Column Superdex-200, buffer: 2 mM HEPES, pH 7.2; 0.1M NaCl; 5 mM $MgCl_2$; 0.1 mM $ZnCl_2$. Two fractions were collected, one with the product and one with the residue.

In comparison to the experiment described above, another conjugate was made with extended conjugation time. The three components below were mixed together and placed in a water bath at 40° C. for 30 minutes.

| 192.0 µL DexVS70 | 13.7 nmol |
|---|---|
| 41.0 µL PNA | 41 nmol PNA dissolved in $H_2O$ |
| 6.0 µL 1M $NaHCO_3$ | |

108.0 µL of the DexVS70-PNA conjugate was taken out and added to a mixture of:

| 160.0 µL AP | 43.4 nmol |
|---|---|
| 7.7 µL 1M $NaHCO_3$ | |
| 30.6 µL 20 mM Hepes, pH 7.2; 1M NaCl; 50 mM $MgCl_2$; 1 mM $ZnCl_2$ | |

The mixture was placed in a water bath at 40° C. for 5 hours. Quenching was performed by adding 30.6 μL 0.1M Ethanolamine and letting the mixture stand for 30 minutes in water bath at 40° C. Purification of the product on FPLC: Column Superdex-200, buffer: 2 mM Hepes, pH 7.2; 0.1M NaCl; 5 mM MgCl$_2$; 0.1 mM ZnCl$_2$. Two fractions were collected: One with the product and one with the residue.

Relative absorbance PNA(Flu) ($\epsilon_{500nm}$=73000M$^{-1}$) and AP ($\epsilon_{278nm}$=140000M$^{-1}$. Corrected for absorbance from PNA at 278 nm, this correction factor is due to the specific PNA and it is calculated: 278/500 nm) was used to calculate the average conjugation ratio of PNA, AP and DexVS70.

AP-DexVS70-PNA, 3 hrs:
PNA/DexVS70: 1.8
AP/DexVS70: 1.8
AP-DexVS70-PNA, 5 hrs:
PNA/DexVS70: 2.0
AP/DexVS70: 2.4

Due to these results, it is recommended to follow a procedure in which the conjugation time (AP+DexVS70-PNA) is 5 hours.

Example 28

Method of Synthesizing Mono and 2,4-diamino-pyrimidine-5-yl PNA Monomers 2,4-diamino-pyrimidine-5-yl may be introduced into DNA-oligomers by methods known in the art (e.g. S. A. Benner et al., *Nucleic Acid Research* 24(7): 1308-1313 (1996)). A corresponding PNA oligomer is prepared by chlorinating pyrimidine-5-acetic acid to yield 2-chloro-pyrimidine-5-acetic acid, 4-chloro-pyrimidine-5-acetic acid, and 2,4-dichloro-pyrimidine-5-acetic acid. Separation of isomers, followed by high temperature and pressure treatment with ammonia, gives the three corresponding amino-pyrimidine derivatives (see FIG. 7). The amino-pyrimidine derivatives are separated and amino-protected, then coupled to a protected PNA backbone ester. Ester hydrolysis results in PNA monomers for production of PNA oligomers containing 2-amino; 4-amino; and/or 2,4-diamino pyrimidine-5-yl bases.

Example 29

Synthesis of Xanthine and Thio-Xanthine-Coupled PNA Monomers

Xanthine, 2-thio-xanthine, and 6-thio-xanthine are commercially available, for instance, from ScienceLab.com. Further, S. A. Benner et al., *Nucleic Acid Research* 24(7): 1308-1313 (1996) teaches the preparation of a xanthosine-DNA monomer, including a less acidic and preferable 7-deaza analog, and notes the preferred protection of both oxygens during solid phase synthesis.

Xanthine PNA-monomers, as well as 2-thio and 6-thio xanthine monomers, are prepared by:

1. Protecting both oxygens or both oxygen and sulphur with appropriate protection groups such as (possibly substituted) benzyl.
2. Alkylating at N-9 with ethyl bromoacetate. (Separating N-7 alkylated byproduct.)
3. Hydrolyzing the ethyl ester.
4. HBTU or Carbodiimide-mediated coupling of the nucleobase-acids to 2-Boc-aminoethyl-ethylglycinate.
5. Hydrolyzing the resulting monomer ester to the monomer free acid.
6. The resulting monomers may be used in Merrifield solid phase synthesis of xanthine, 2-thio-xanthine and 6-thio-xanthine-containing PNAs.

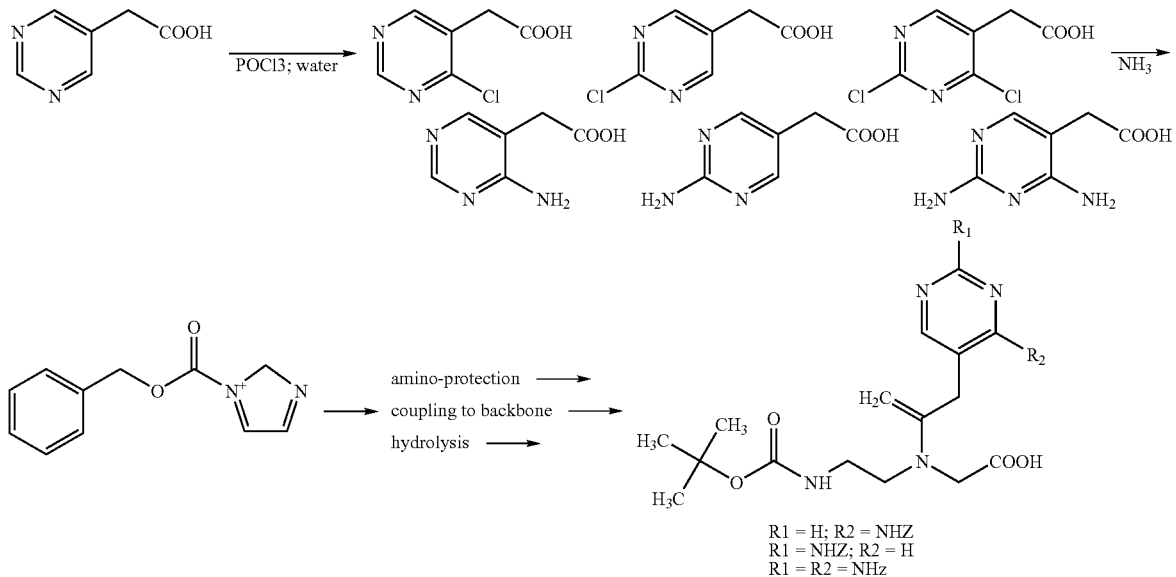

R1 = H; R2 = NHZ
R1 = NHZ; R2 = H
R1 = R2 = NHz

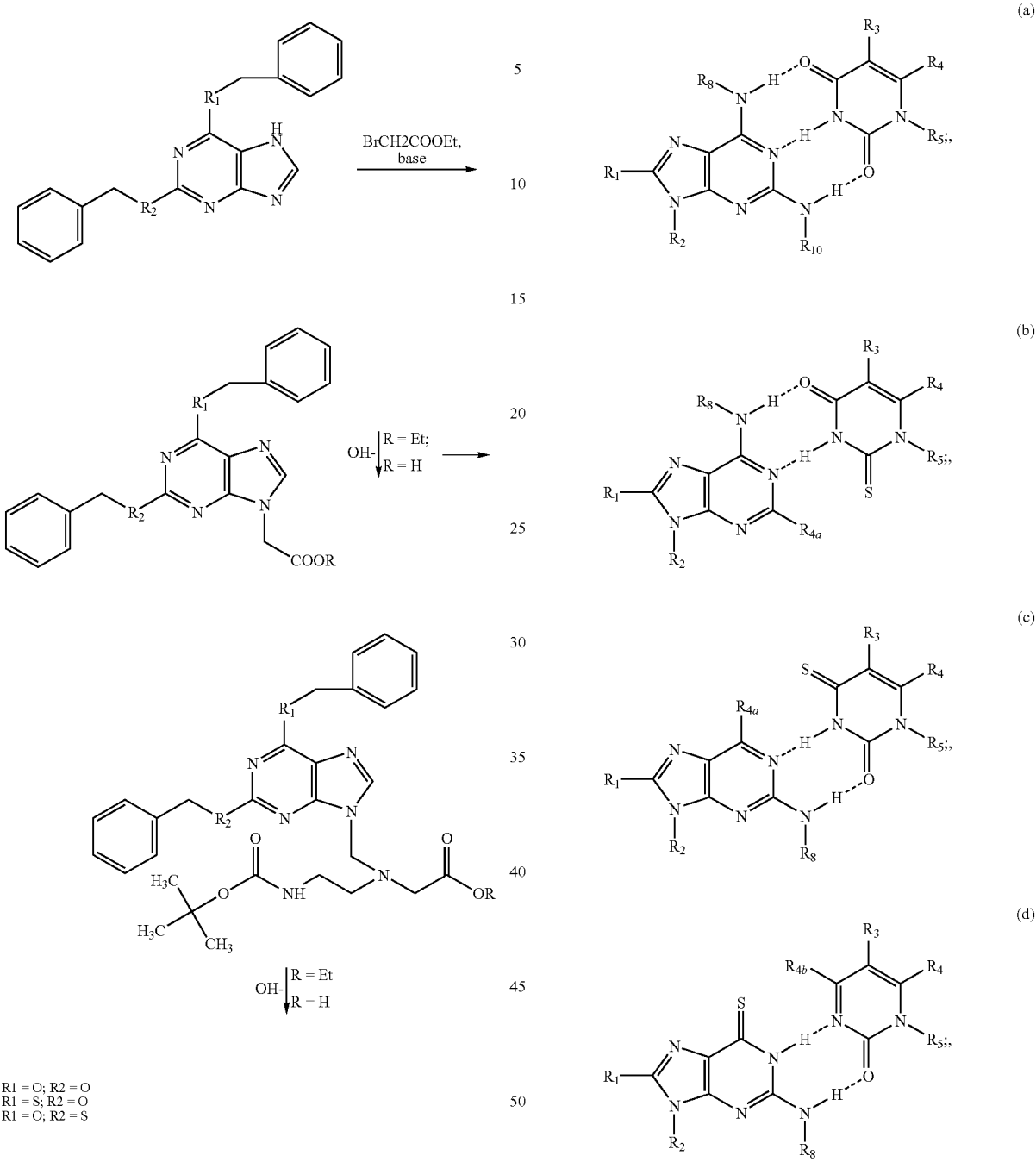

R1 = O; R2 = O
R1 = S; R2 = O
R1 = O; R2 = S

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition comprising a pair of PNA oligomers which
   i) hybridize to each other through base-pairing that comprises more than one of the following combinations:

-continued
(f) 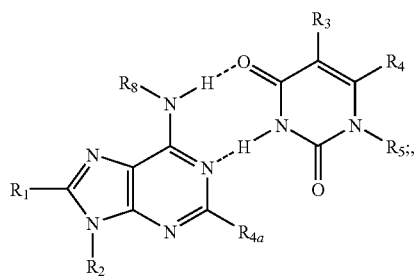
(g) 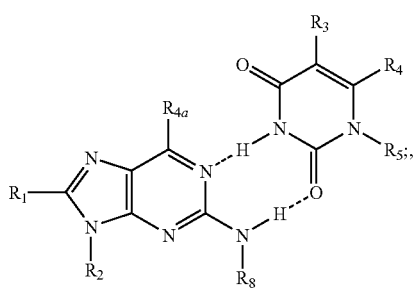
(h) 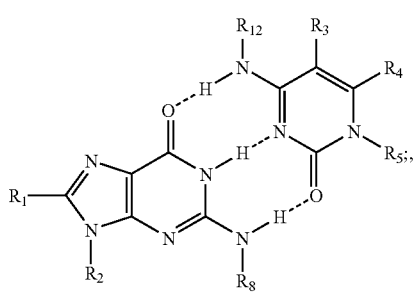
(i) 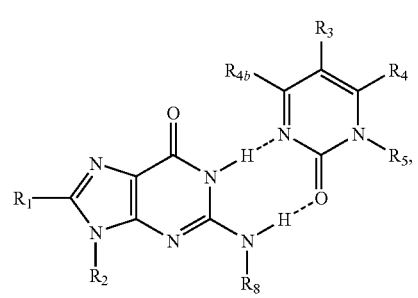
(j) 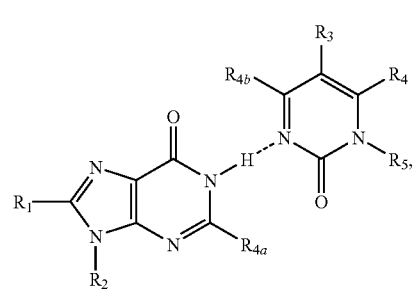
-continued
(k) 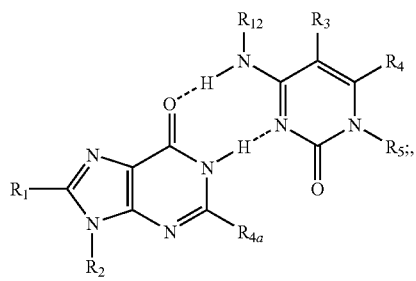
(l) 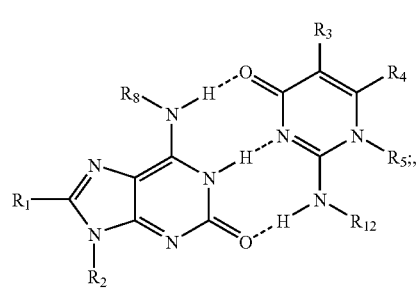
(m) 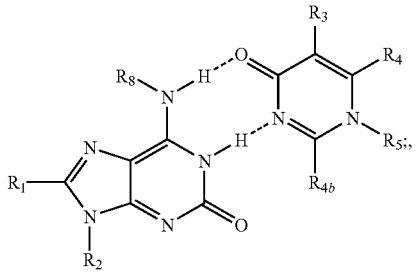
(n) 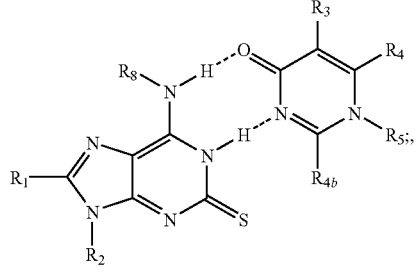
(o) 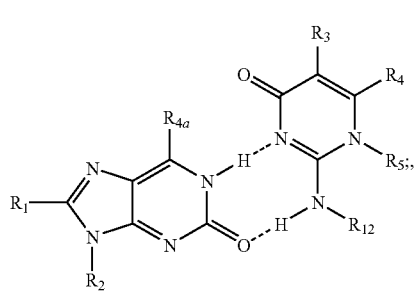

-continued

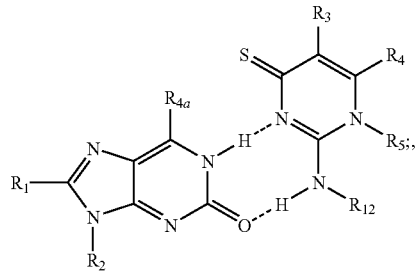
(p)

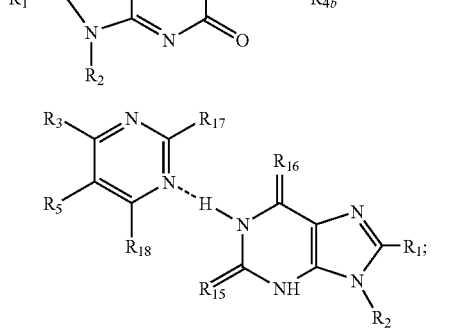
(q)

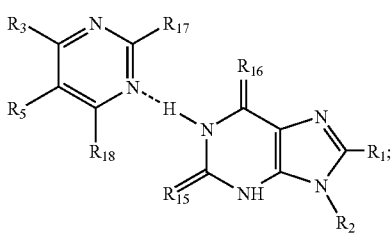
(r)

wherein:
R$_1$ is chosen from hydrogen, halogen, substituted (C$_1$-C$_4$)-alkyl, unsubstituted (C$_1$-C$_4$)-alkyl, —NR$_6$R$_7$, substituted (C$_1$-C$_4$)-alkoxy, unsubstituted (C$_1$-C$_4$)-alkoxy, substituted (C$_3$-C$_6$)-cycloalkyl, unsubstituted (C$_3$-C$_6$)-cycloalkyl linker, a polyamide backbone, and linker bound to a polyamide backbone;

R$_2$ is chosen from hydrogen, substituted (C$_1$-C$_4$)-alkyl, unsubstituted (C$_1$-C$_4$)-alkyl, —NR$_6$R$_7$, substituted (C$_1$C$_4$)-alkoxy, unsubstituted (C$_1$C$_4$)-alkoxy, substituted (C$_3$-C$_6$)-cycloalkyl, unsubstituted (C$_3$-C$_6$)-cycloalkyl, linker, a polyamide backbone, and linker bound to a polyamide backbone;

R$_3$ is group chosen from hydrogen, halogen, substituted (C$_1$-C$_{20}$)-alkyl, unsubstituted (C$_1$-C$_{20}$)-alkyl, —NR$_6$R$_7$, substituted (C$_1$-C$_{20}$)-alkoxy, unsubstituted (C$_1$-C$_{20}$)-alkoxy, substituted (C$_3$-C$_8$)-cycloalkyl, unsubstituted (C$_3$-C$_8$)-cycloalkyl, linker, a polyamide backbone, and linker bound to a polyamide backbone;

R$_4$ is chosen from hydrogen, halogen, substituted (C$_1$-C$_4$)-alkyl, unsubstituted (C$_1$-C$_4$)-alkyl, —NR$_6$R$_7$, substituted (C$_1$-C$_4$)-alkoxy, unsubstituted (C$_1$-C$_4$)-alkoxy, substituted (C$_3$-C$_6$)-cycloalkyl, unsubstituted (C$_3$-C$_6$)-cycloalkyl, linker, a polyamide backbone, and linker bound to a polyamide backbone;

R$_{4a}$ is chosen from hydrogen, fluorine and chlorine;
R$_{4b}$ is chosen from hydrogen, fluorine, and chlorine;
R$_5$ is chosen from hydrogen, substituted (C$_1$-C$_4$)-alkyl, unsubstituted (C$_1$-C$_4$)-alkyl, —NR$_6$R$_7$, substituted (C$_1$-C$_4$)-alkoxy, unsubstituted (C$_1$-C$_4$)-alkoxy, substituted (C$_3$-C$_6$)-cycloalkyl, unsubstituted (C$_5$-C$_6$)-cycloalkyl, linker, a polyamide backbone, and linker bound to a polyamide backbone;

R$_6$ and R$_7$ can be identical or different, and are chosen from hydrogen, substituted (C$_1$-C$_{20}$)-alkyl, and unsubstituted (C$_1$-C$_{20}$)-alkyl;

R$_8$ and R$_{12}$ can be identical or different, and are chosen from hydrogen, halogen,

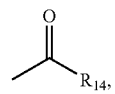

substituted (C$_1$-C$_{20}$)-alkoxy, unsubstituted (C$_1$-C$_{20}$)-alkoxy, substituted (C$_3$-C$_8$)-cycloalkyl, unsubstituted (C$_3$-C$_8$)-cycloalkyl, substituted (C$_1$-C$_{20}$)-alkyl, and unsubstituted (C$_1$-C$_{20}$)-alkyl; and R$_{14}$ is chosen from hydrogen, substituted (C$_1$-C$_{20}$)-alkyl, unsubstituted (C$_1$-C$_{20}$)-alkyl, substituted (C$_1$-C$_{20}$)-alkoxy, unsubstituted (C$_1$-C$_{20}$)-alkoxy, substituted (C$_3$-C$_8$)-cycloalkyl, and unsubstituted (C$_3$-C$_8$)-cycloalkyl;

R$_{15}$ and R$_{16}$ are chosen from oxygen and sulfur;
R$_{17}$ and R$_{18}$ are chosen from hydrogen and —NH$_2$; and (ii) do not interfere with RNA or DNA.

2. The composition according to claim 1, wherein R$_1$, R$_3$, and R$_4$ each is hydrogen.

3. The composition according to claim 1, wherein R$_2$ and R$_5$ can be identical or different and are chosen from linker, a polyamide backbone, and linker bound to a polyamide backbone.

4. The composition according to claim 1, wherein:
R1, R3, and R4 each is hydrogen;
R2 and R5 can be identical or different and are chosen from a polyamide backbone and linker bound to polyamide backbone.

5. The composition according to claim 1, wherein the base pairing comprises at least two hydrogen bonds.

6. The composition according to claim 5, wherein the base pairing comprises three hydrogen bonds.

7. The composition according to claim 1, wherein the base pairing comprises a Watson Crick-type hydrogen bonding geometry or a Hoogsteen-type hydrogen bonding geometry.

8. The composition of claim 1 wherein at least one of the PNA oligomers further comprises a polymer.

9. The composition of claim 8 wherein the polymer is dextran.

10. The composition of claim 1, wherein at least one of the PNA oligomers comprises a linker.

11. The composition according to claim 10, wherein the linker is chosen from a molecule comprising polyethylene glycol and a molecule comprising at least two units according to the Formula 1:

Formula I

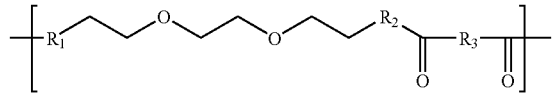

wherein $R_1$ and $R_2$ comprise NH or O, and $R_3$ comprises methyl, ethyl, propyl, $CH_2$—O—$CH_2$, and ($CH_2$—O—$CH_2$)$_2$.
12. A composition comprising a pair of PNA oligomers which (i) hybridize to each other through base-pairing and (ii) do not interfere with RNA or DNA,
wherein at least one of the PNA oligomers comprises at least one molecule chosen from:
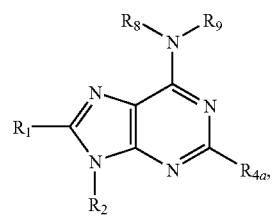
(1)
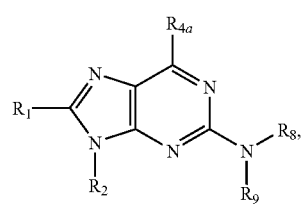
(2)
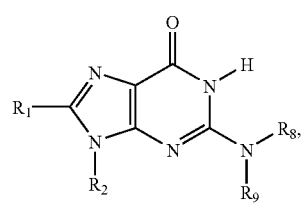
(3)
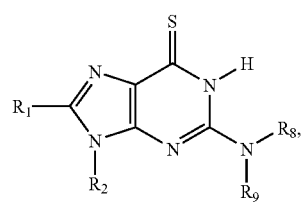
(4)
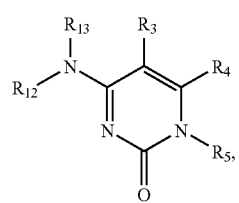
(5)
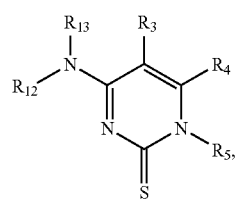
(6)
-continued
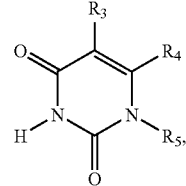
(7)
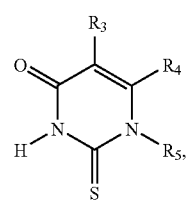
(8)
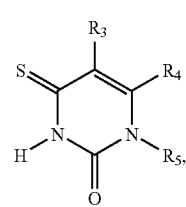
(9)
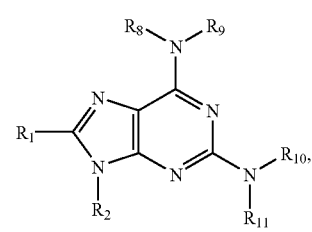
(10)
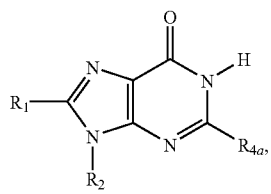
(11)
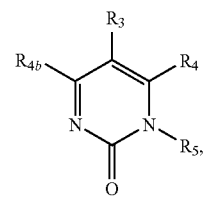
(12)
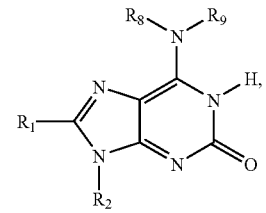
(13)

(14) 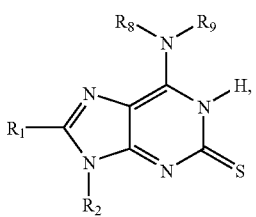

(15) 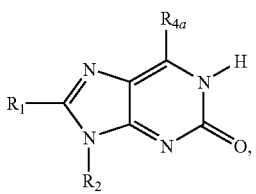

(16) 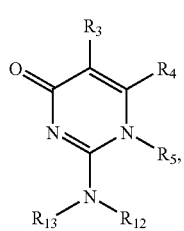

(17) 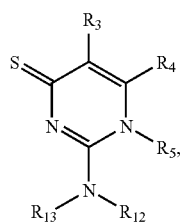

(18) 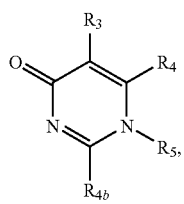

(19) 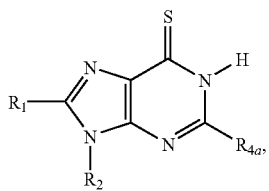

(20) 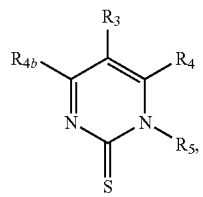

(21) 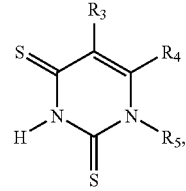

(22) 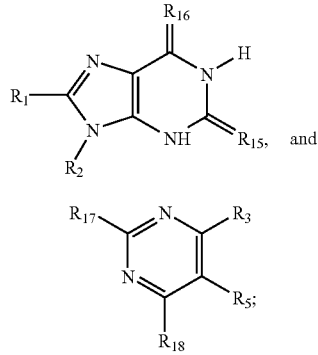 and (23)

wherein $R_1$ is chosen from hydrogen, halogen, substituted $(C_1-C_4)$-alkyl, unsubstituted $(C_1-C_4)$-alkyl, —$NR_6R_7$, substituted $(C_1-C_4)$-alkoxy, unsubstituted $(C_1-C_4)$-alkoxy, substituted $(C_3-C_6)$-cycloalkyl, unsubstituted $(C_3-C_6)$-cycloalkyl linker, a polyamide backbone, and linker bound to a polyamide backbone; wherein:

$R_2$ is chosen from hydrogen, substituted (C1-C4)-alkyl, unsubstituted (C1-C4)-alkyl, —NR6R7, substituted (C1C4)-alkoxy, unsubstituted (C1C4)-alkoxy, substituted (C3-C6)-cycloalkyl, unsubstituted (C3-C6)-cycloalkyl, linker, a polyamide backbone, and linker bound to a polyamide backbone;

R3 is group chosen from hydrogen, halogen, substituted (C1-C20)-alkyl, unsubstituted (C1-C20)-alkyl, —NR6R7, substituted (C1-C20)-alkoxy, unsubstituted (C1-C20)-alkoxy, substituted (C3-C8)-cycloalkyl, unsubstituted (C3-C8)-cycloalkyl, linker, a polyamide backbone, and linker bound to a polyamide backbone;

R4 is chosen from hydrogen, halogen, substituted (C1-C4)-alkyl, unsubstituted (C1-C4)-alkyl, —NR6R7, substituted (C1-C4)-alkoxy, unsubstituted (C1-C4)-alkoxy, substituted (C3-C6)-cycloalkyl, unsubstituted (C3-C6)-cycloalkyl, linker, a polyamide backbone, and linker bound to a polyamide backbone;

$R_{4a}$ is chosen from hydrogen, fluorine and chlorine;

$R_{4b}$ is chosen from hydrogen, fluorine, and chlorine;

R5 is chosen from hydrogen, substituted (C1-C4)-alkyl, unsubstituted (C1-C4)-alkyl, —NR6R7, substituted (C1-C4)-alkoxy, unsubstituted (C1-C4)-alkoxy, substituted (C3-C6)-cycloalkyl, unsubstituted (C5-C6)-cycloalkyl, linker, a polyamide backbone, and linker bound to a polyamide backbone;

R6 and R7 can be identical or different, and are chosen from hydrogen, substituted (C1-C20)-alkyl, and unsubstituted (C1-C20)-alkyl;

R8 and, R12 can be identical or different, and are chosen from hydrogen, halogen,

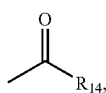

substituted (C1-C20)-alkoxy, unsubstituted (C1-C20)-alkoxy, substituted (C3-C8)-cycloalkyl, unsubstituted (C3-C8)-cycloalkyl, substituted (C1-C20)-alkyl, and unsubstituted (C1-C20)-alkyl;

R14 is chosen from hydrogen, substituted (C1-C20)-alkyl, unsubstituted (C1-C20)-alkyl, substituted (C1-C20)-alkoxy, unsubstituted (C1-C20)-alkoxy, substituted (C3-C8)-cycloalkyl, and unsubstituted (C3-C8)-cycloalkyl;

R15 and R16 are chosen from oxygen and sulfur; and

R17 and R18 are chosen from hydrogen and —NH2.

13. The composition according to claim 12, wherein $R_1$, $R_3$, and $R_4$ each is hydrogen.

14. The composition according to claim 12, wherein $R_2$ and $R_5$ can be identical or different and are chosen from linker, backbone, and linker bound to backbone.

15. The composition according to claim 12, wherein:

$R_1$, $R_3$, and $R_4$ each is hydrogen;

$R_2$ and $R_5$ can be identical or different and are chosen from a polyamide backbone and linker bound to polyamide backbone.

16. The composition of claim 12, wherein at least one of the PNA oligomers further comprises a polymer.

17. The composition of claim 16, wherein the polymer is dextran.

18. The composition of claim 10, wherein at least one of the PNA oligomers comprises a linker.

19. The composition according to claim 18, wherein the linker is chosen from a molecule comprising polyethylene glycol and a molecule comprising at least two units according to the Formula 1:

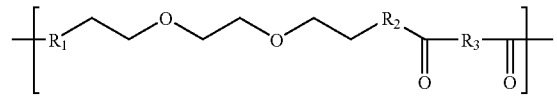

Formula I wherein R1 and R2 comprise NH or O, and R3 comprises methyl, ethyl, propyl, CH2-O—CH2, and (CH2-O—CH2)2.

20. The composition of claim 8 wherein the polymer is selected from polysaccharides, pullulans, chitins, chitosans, derivatized cellolosics, hydroxylated starch, carrageenans, alginates, agarose, synthetic polysaccharides, vinyl polymers, polyethylene glycols with polymer backbones, polypropylene glycols with polymer backbones, poly(ethylene oxide-co-propylene oxides) with polymer backbones, poly amino acids, proteins, and polynucleotides.

21. The composition of claim 16 wherein the polymer is selected from polysaccharides, pullulans, chitins, chitosans, derivatized cellolosics, hydroxylated starch, carrageenans, alginates, agarose, synthetic polysaccharides, vinyl polymers, polyethylene glycols with polymer backbones, polypropylene glycols with polymer backbones, poly(ethylene oxide-co-propylene oxides) with polymer backbones, poly amino acids, proteins, and polynucleotides.

* * * * *